United States Patent
Gaber

[11] Patent Number: 5,810,861
[45] Date of Patent: Sep. 22, 1998

[54] UTERINE TISSUE COLLECTOR

[76] Inventor: Benny Gaber, 29 Oren Street, Haifa 34735, Israel

[21] Appl. No.: 607,901

[22] Filed: Feb. 27, 1996

[30] Foreign Application Priority Data

Mar. 2, 1995 [IL] Israel ......................................... 112865
Aug. 13, 1995 [IL] Israel ......................................... 114920

[51] Int. Cl.⁶ .................................................. A61B 10/00
[52] U.S. Cl. .......................................................... 600/571
[58] Field of Search ..................................... 128/749–759

[56] References Cited

U.S. PATENT DOCUMENTS

| | | |
|---|---|---|
| 2,495,794 | 1/1950 | Weller ..................... 128/757 |
| 3,491,747 | 1/1970 | Robinson ................. 128/757 |
| 4,010,737 | 3/1977 | Vilaghy et al. . |
| 4,311,140 | 1/1982 | Bridgman . |
| 4,340,066 | 7/1982 | Shah . |
| 4,895,166 | 1/1990 | Farr et al. . |
| 4,921,482 | 5/1990 | Hammerslag et al. . |
| 4,998,916 | 3/1991 | Hammerslag et al. . |
| 5,037,391 | 8/1991 | Hammerslag et al. . |
| 5,108,368 | 4/1992 | Hammerslag et al. . |
| 5,176,646 | 1/1993 | Kuroda . |
| 5,217,024 | 6/1993 | Dorsey et al. ............... 128/249 |
| 5,217,479 | 6/1993 | Shuler . |
| 5,224,488 | 7/1993 | Neuffer . |
| 5,301,684 | 4/1994 | Ogirala ..................... 128/754 |
| 5,335,671 | 8/1994 | Clement . |
| 5,469,860 | 11/1995 | De Santis ................. 128/754 |
| 5,505,210 | 4/1996 | Clement ................... 128/153 |
| 5,620,415 | 4/1997 | Lucey et al. .............. 128/752 |

FOREIGN PATENT DOCUMENTS 2602414 2/1988 France .
80/1351 3/1980 South Africa .

OTHER PUBLICATIONS

Pipelle De Cornier, "Endometrial Suction Curette", Prodimed. (brochure), 1984.

*Primary Examiner*—Max Hindenburg
*Assistant Examiner*—Pamela L. Wingood
*Attorney, Agent, or Firm*—Helfgott & Karas, P.C.

[57] ABSTRACT

A uterine tissue collector including a deformable scraper which scrapes a uterus, a deformer which deforms the deformable scraper, and a suction device which sucks material scraped by the deformable scraper.

29 Claims, 25 Drawing Sheets

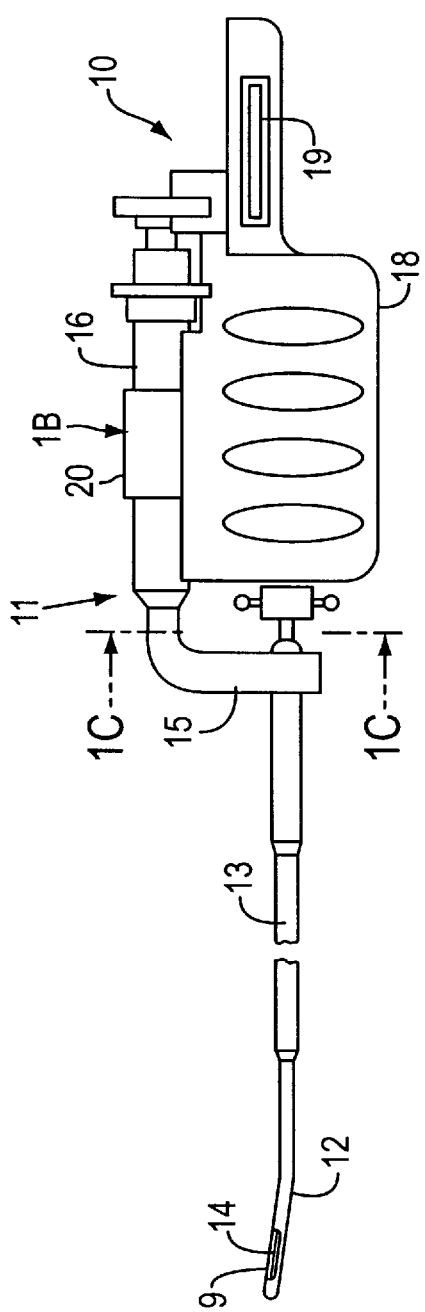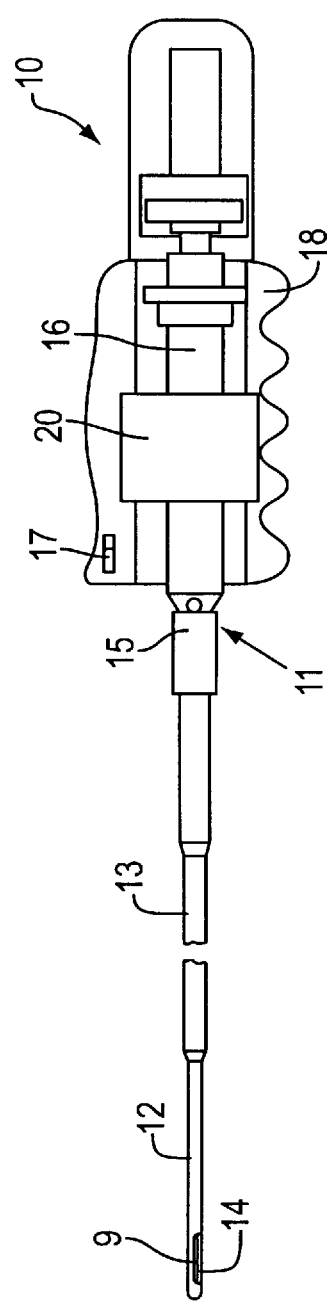

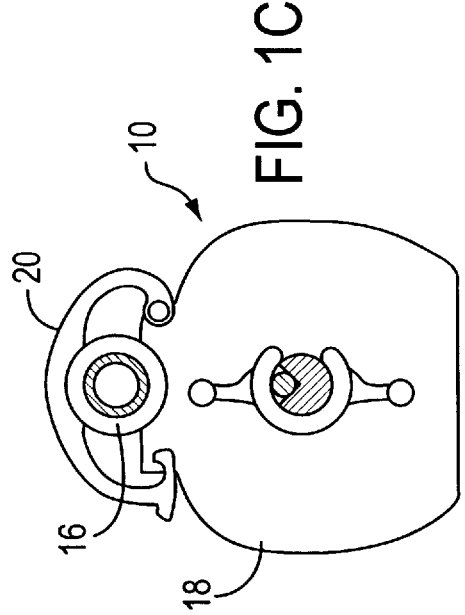
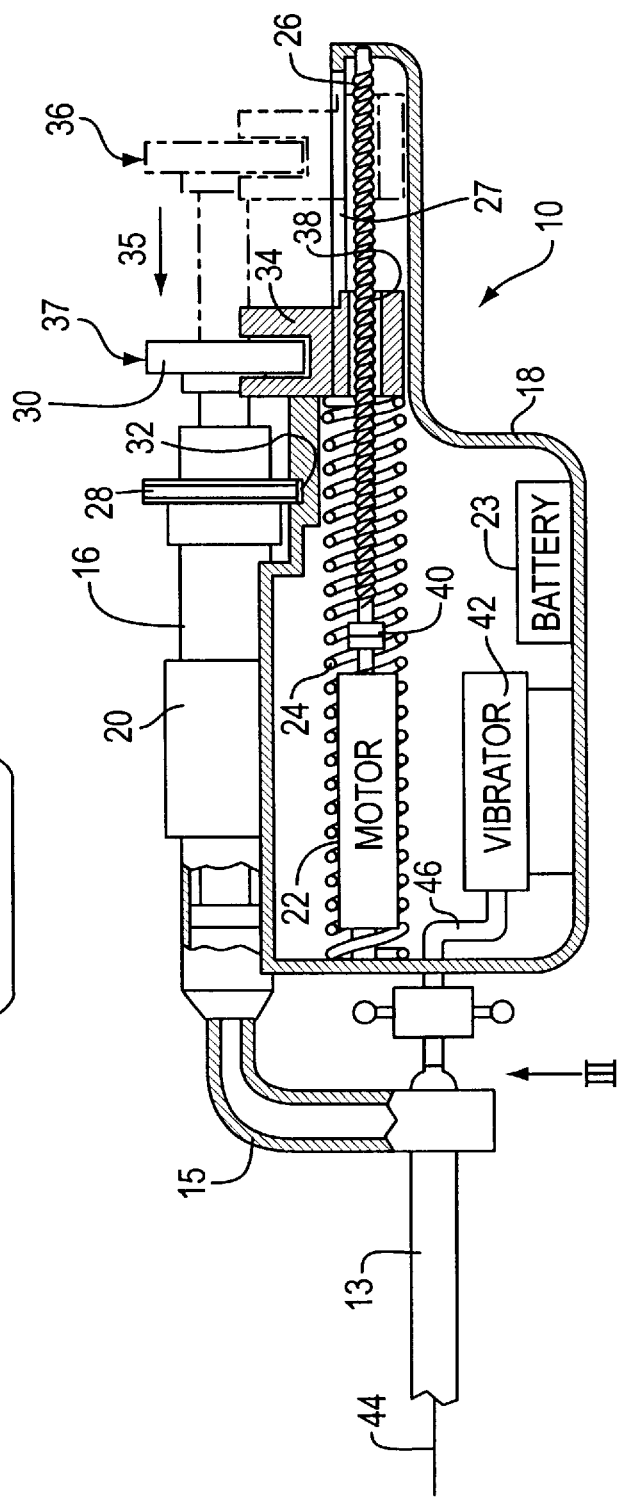

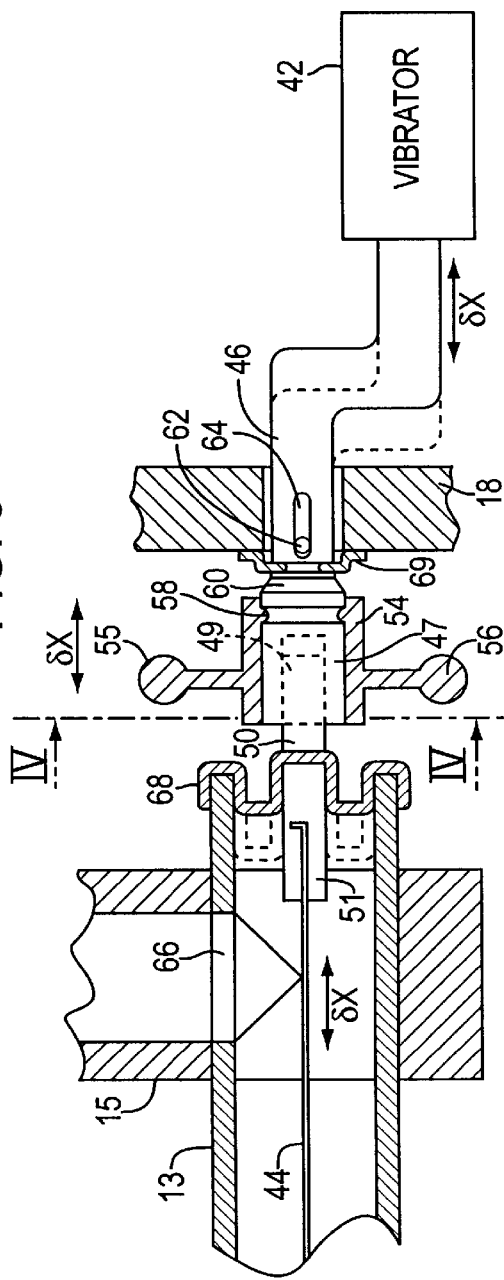
FIG. 3
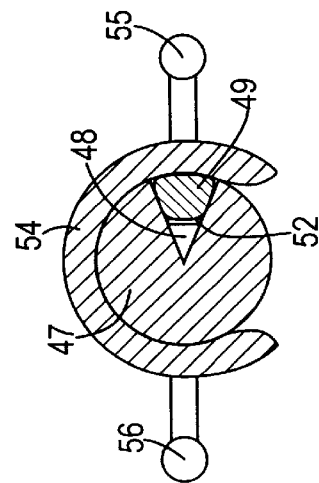
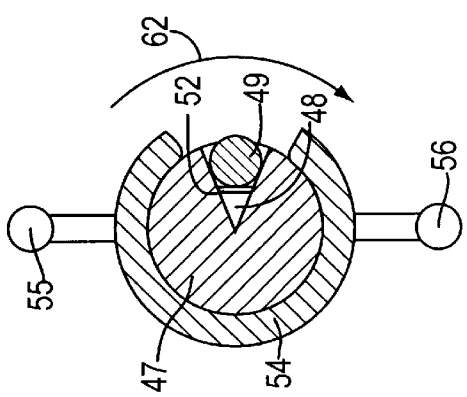
FIG. 4A
FIG. 4B

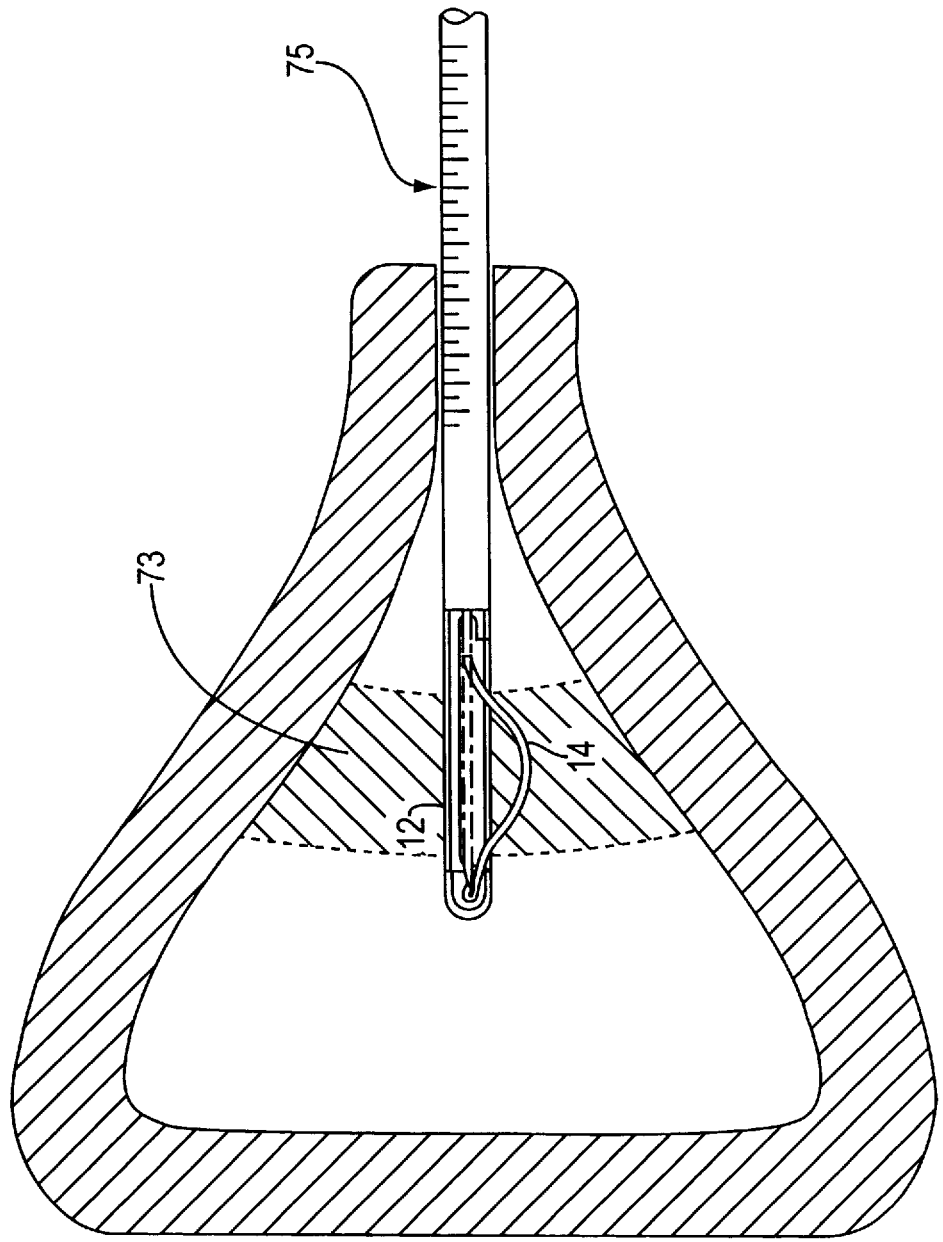

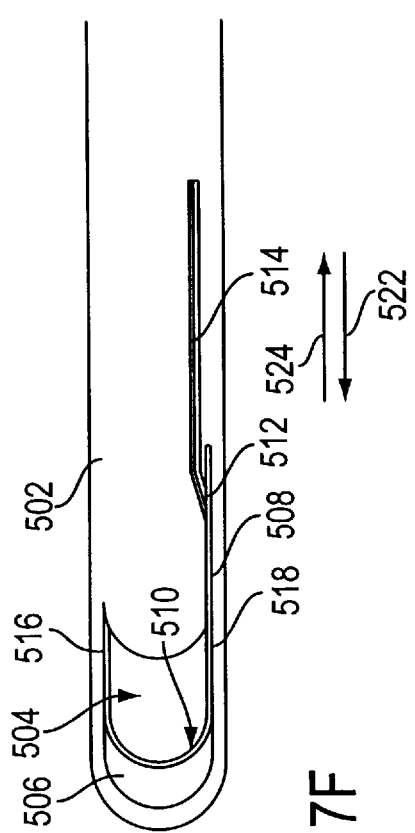
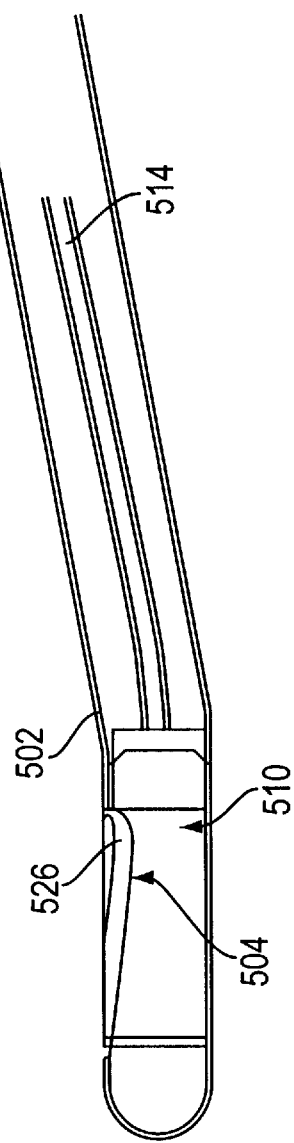
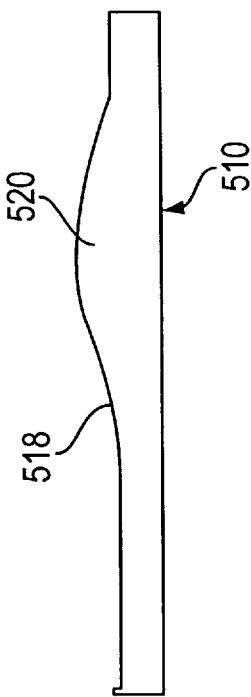
FIG. 7F
FIG. 7G
FIG. 7H

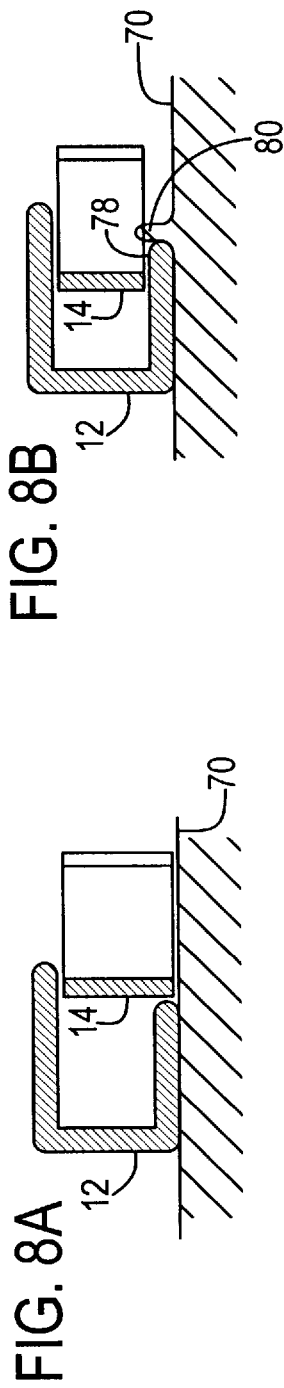
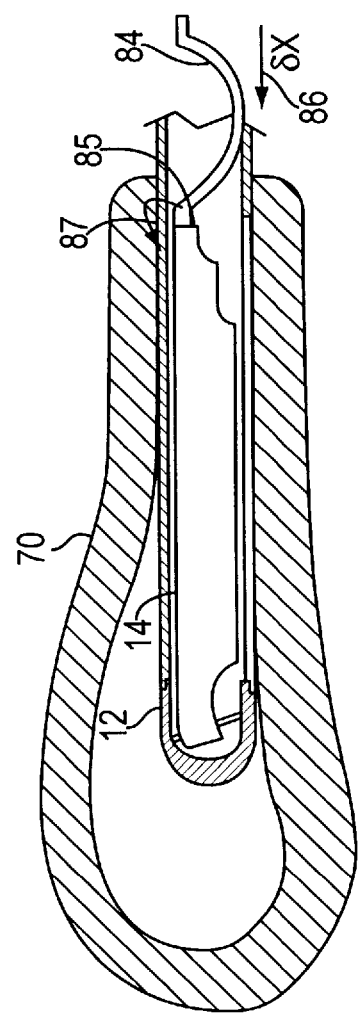
FIG. 8A
FIG. 8B
FIG. 9

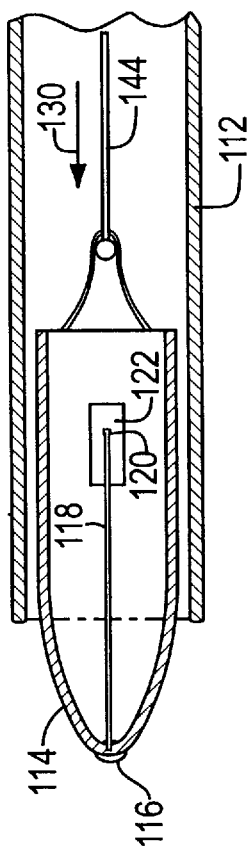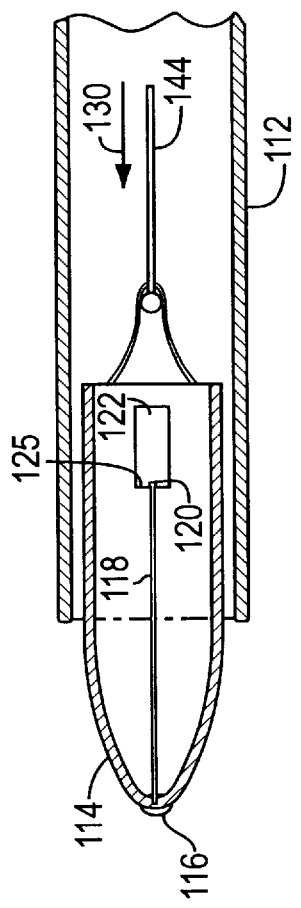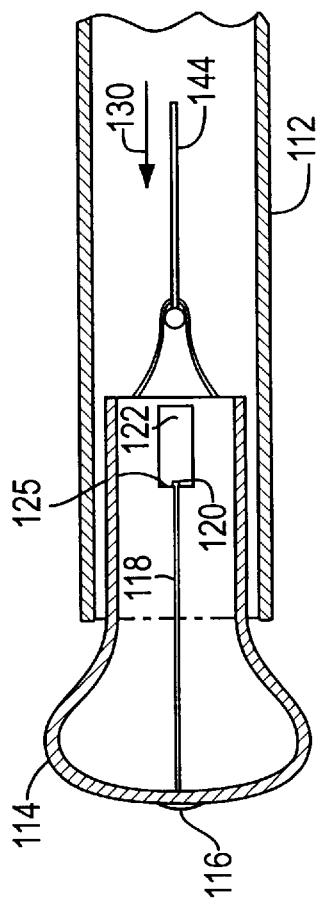

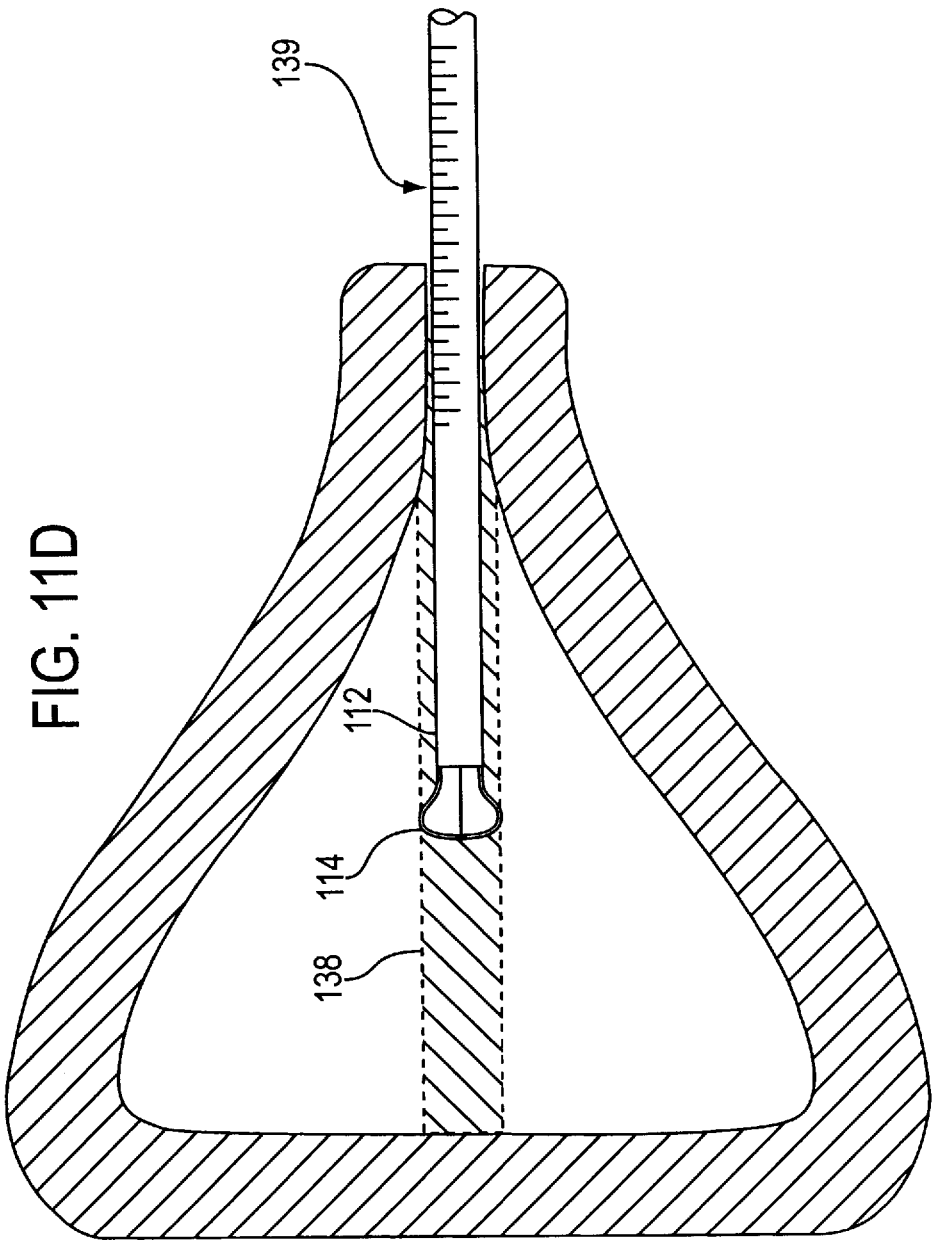

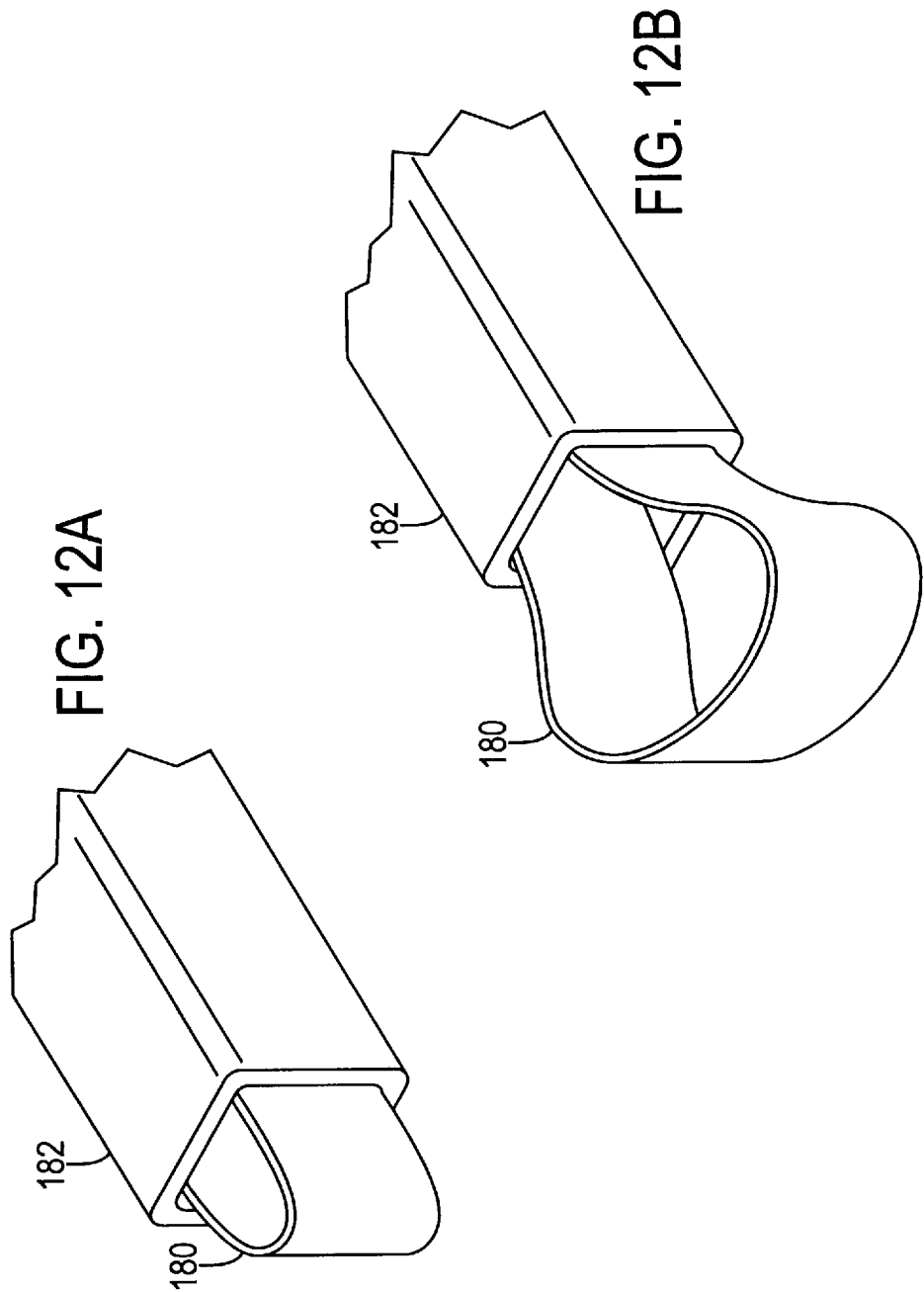

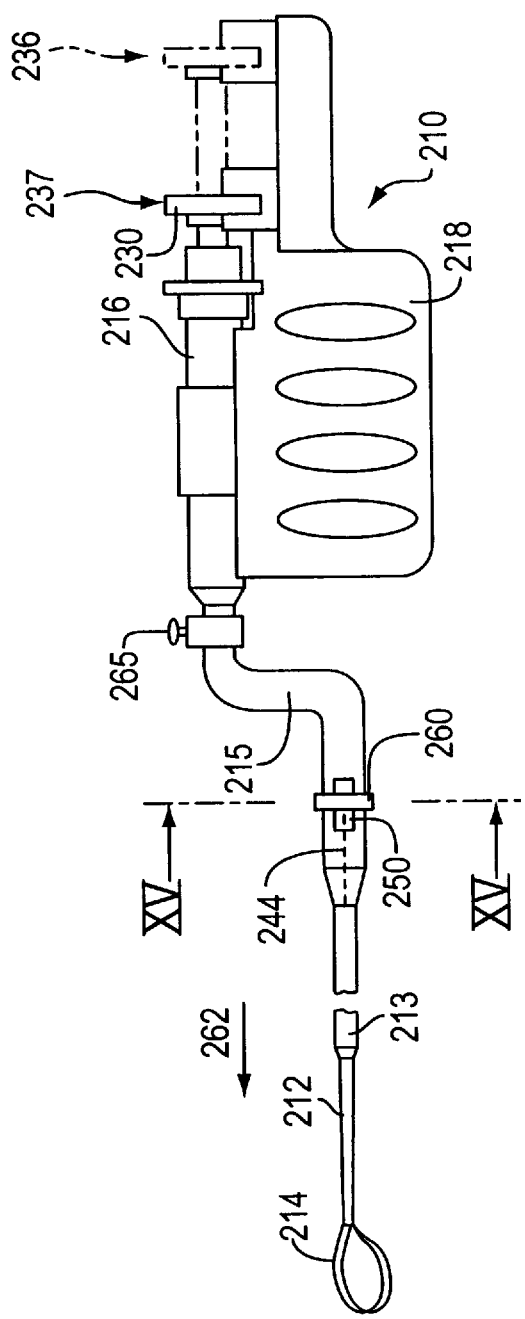

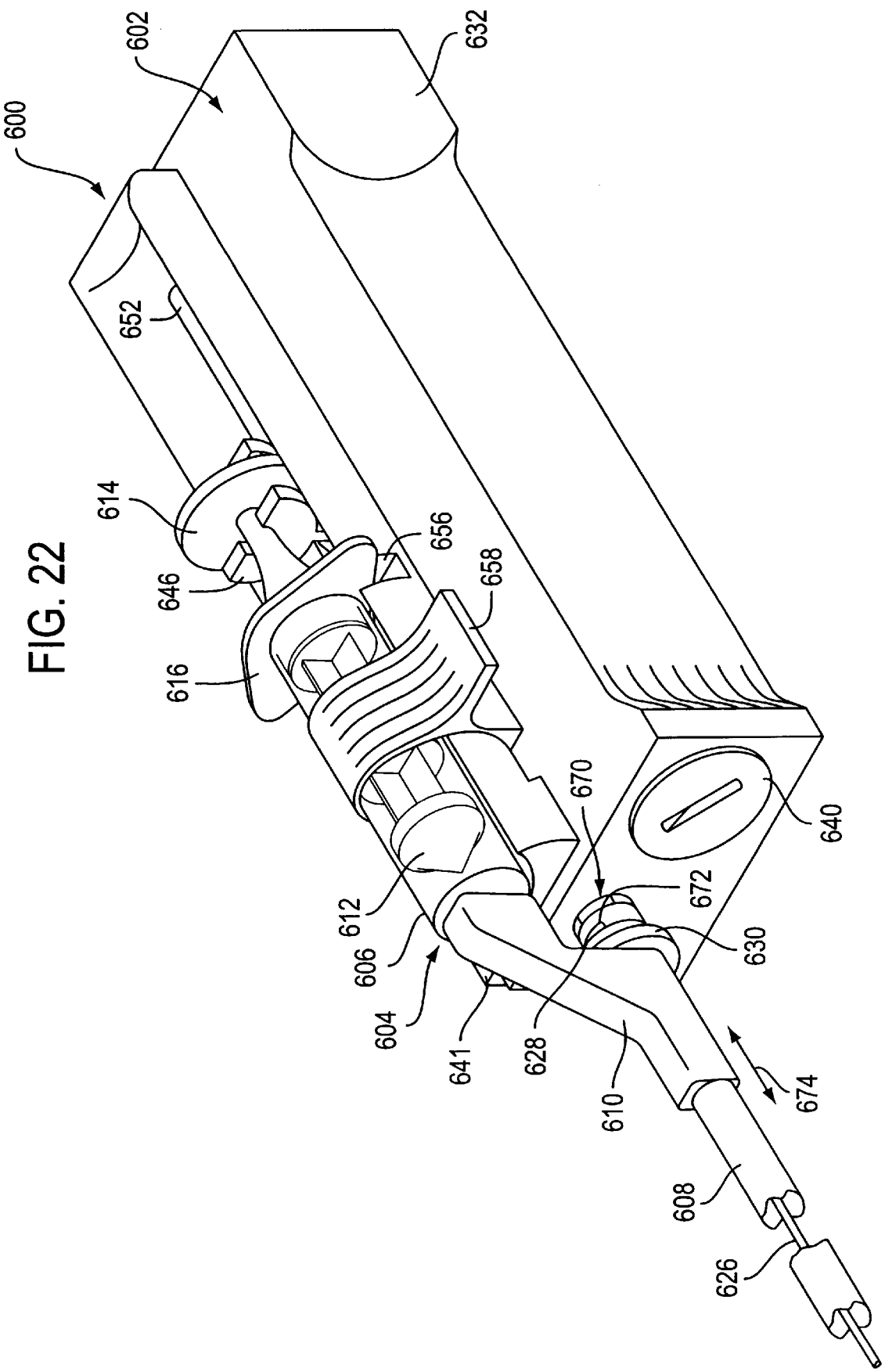

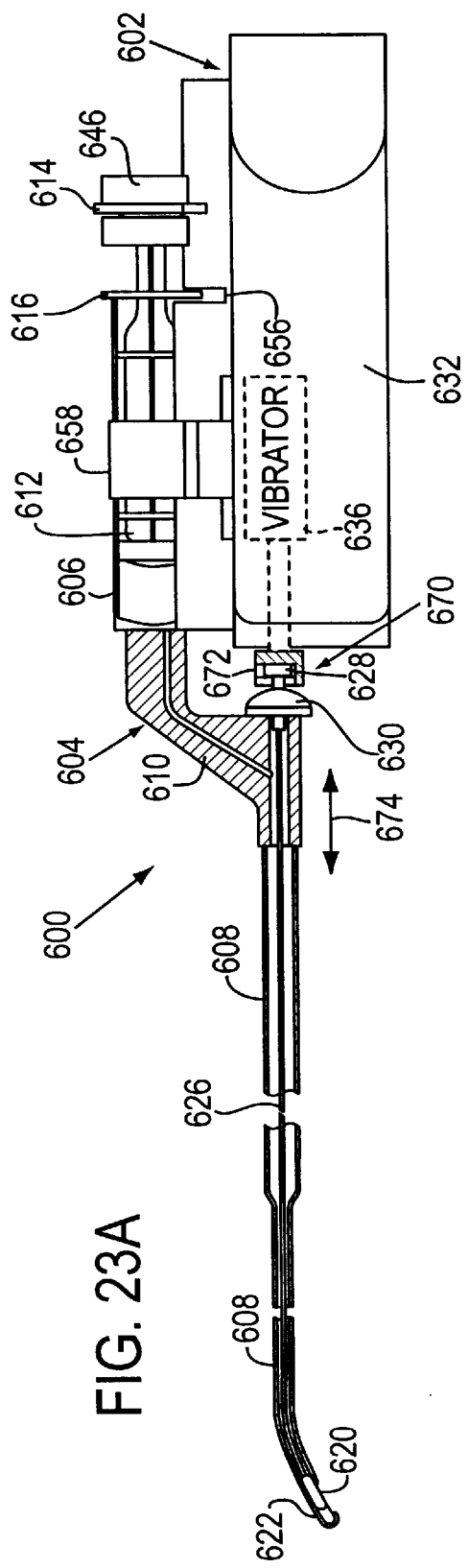
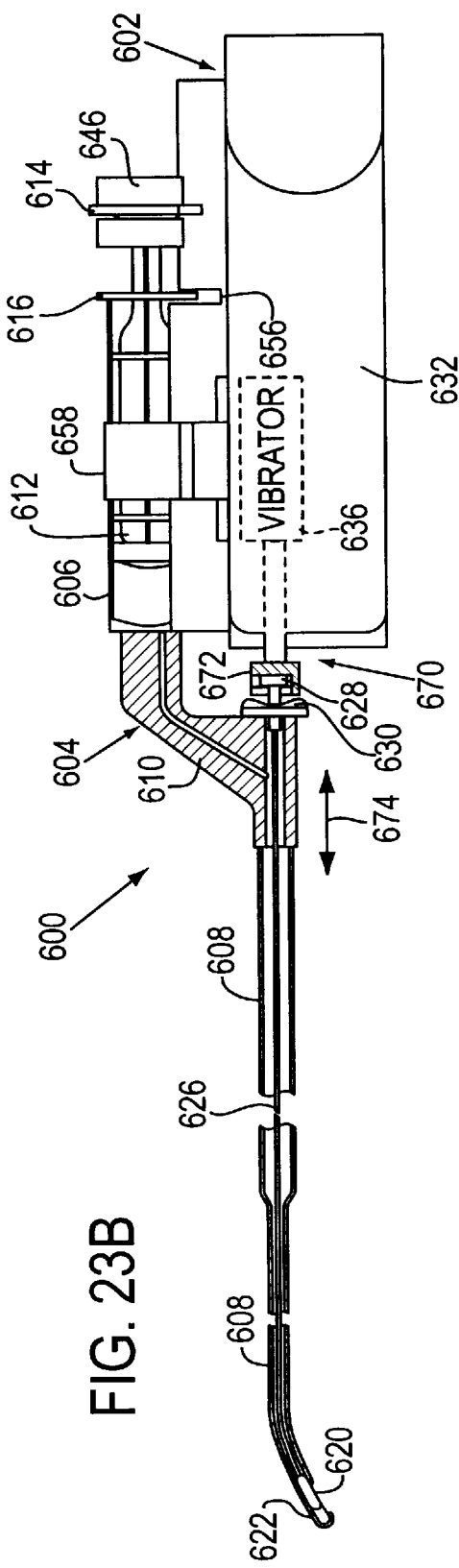
FIG. 23A
FIG. 23B

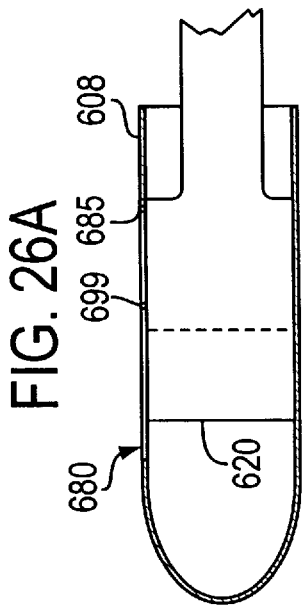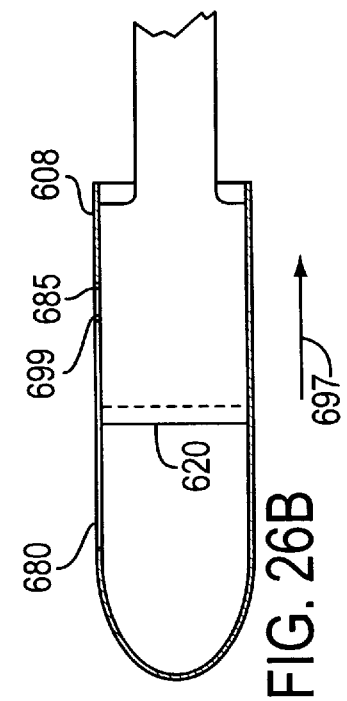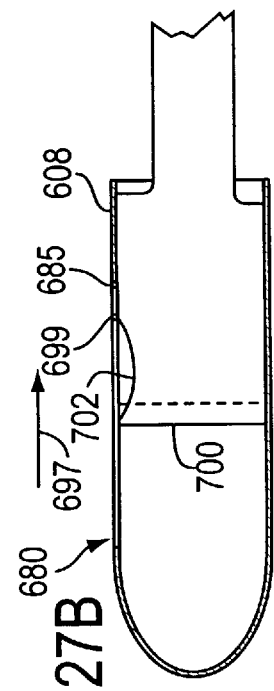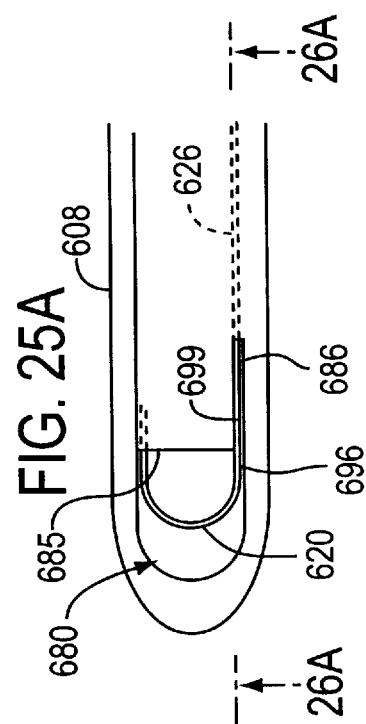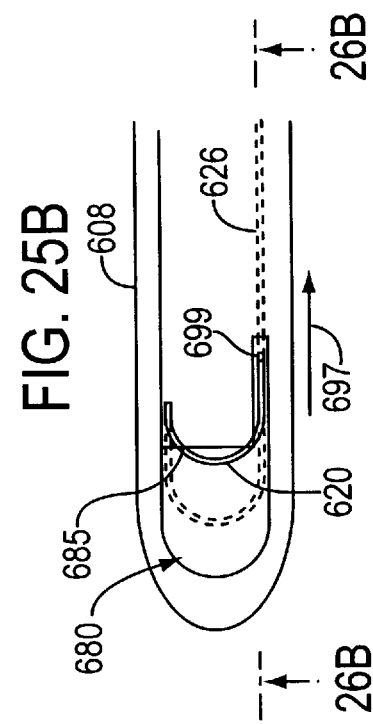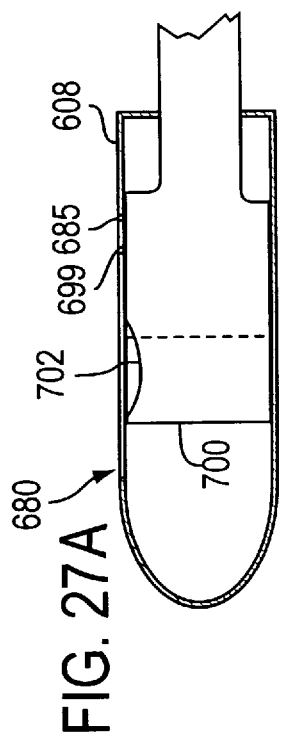

UTERINE TISSUE COLLECTOR

FIELD OF THE INVENTION

The present invention relates to gynecological instruments generally.

BACKGROUND OF THE INVENTION

Obtaining samples of cervical and uterine tissue is normally performed in the art by one of three methods: dilation of the cervix and curettage of the endometrium, known as D & C; suction without dilation of the cervix via a small diameter tube, known as aspiration; or by suction curettage. D & C and suction curettage are capable of collecting as much cervical or uterine material as required, but require anesthesia. Aspiration with a small diameter tube does not normally require anesthesia but is not capable of obtaining amounts of tissue comparable to those obtainable with D & C. In order to obtain amounts of tissue comparable to those obtainable with D & C, aspiration must be performed with a large tube which requires anesthesia.

A recently developed endometrial suction curette, called the Pipelle de Cornier, manufactured by PRODIMED of France, may be used to scrape endometrial material with the distal end of a sheath of the curette. However, the scraping area is limited by the relatively small diameter of the sheath.

SUMMARY OF THE INVENTION

The present invention seeks to provide an instrument for collection of a sufficient amount of uterine tissue without need for dilation of the cervix and anesthesia. The amount of tissue collected is the same as that obtained in D & C.

It is noted that throughout the specification and claims, the term "uterine tissue" refers to any material in the cervical canal and uterine cavity, e.g. uterine layering, cervical mucosa, gestational products, endometrium or tumoral substances. In the specification and claims, the term "uterus" encompasses the cervical canal and uterine cavity.

There is thus provided in accordance with a preferred embodiment of the present invention a uterine tissue collector including a deformable scraper which scrapes a uterus, a deformer which deforms the deformable scraper, and a suction device which sucks material scraped by the deformable scraper.

The present invention includes three basic embodiments of suction devices. The first embodiment sucks automatically, preferably by means of a syringe powered by a motor, preferably in conjunction with a biasing device such as a spring. The second embodiment sucks with an external suction device, preferably a vacuum pump which sucks material via a flexible tube. The third embodiment sucks semi-automatically preferably by means of a syringe, a valve and a biasing device such as a spring.

The present invention includes different embodiments of scrapers which are distinguished by the way they deform, scrape and/or cut. Scraping may be performed automatically with a vibrator such as a solenoid, or it may be performed manually.

In accordance with a preferred embodiment of the present invention, the uterine tissue collector includes a cannula having an aperture, the deformable scraper being disposed in the cannula, such that when the scraper is deformed it protrudes through the aperture and scrapes the uterus.

Preferably the cannula has a substantially rectangular shape towards a rearward end thereof.

It is noted that throughout the specification and claims, rearward refers to a direction towards a posterior or distal end. Forward refers to a direction towards an anterior or proximal end.

In accordance with one preferred embodiment of the present invention, the aperture is on one face of a rearward end of the cannula, the face being adapted to be in contact with the uterus.

In accordance with another preferred embodiment of the present invention, the aperture is open on an additional face of the cannula, such that the scraper may protrude through the additional face.

There is also provided in accordance with a preferred embodiment of the present invention a uterine tissue collector including a deformable scraper which scrapes a uterus, the scraper being slidably attached to an inclined post, such that the scraper is in a deformed configuration at a first end of the inclined post and is in an undeformed configuration at a second end of the inclined post, a deformer which deforms the deformable scraper, and a suction device which sucks and plucks material scraped by the deformable scraper. The scraper scrapes the uterus in a raking motion and the suction device sucks and plucks material from the uterine surface. The scraping and raking motion is substantially lateral and medial, as well as vertical.

In accordance with a preferred embodiment of the present invention, the deformable scraper has a serrated edge.

In a preferred embodiment of the present invention, the cannula has a beveled edge which cuts tissue.

Still further in accordance with a preferred embodiment of the present invention, the deformable scraper deforms from a compressed configuration to a non-compressed configuration.

Additionally in accordance with a preferred embodiment of the present invention, the deformable scraper cuts tissue.

Additionally in accordance with a preferred embodiment of the present invention, the aperture is radially deeper in a direction away from a rearward tip of the cannula.

Additionally in accordance with a preferred embodiment of the present invention, the scraper is generally U-shaped. The scraper may also have an arcuate protrusion.

In accordance with a preferred embodiment of the present invention, the deformer includes a wire coupled to the deformable scraper.

It is noted that throughout the specification and the claims, the term "wire" refers to any relatively slender, relatively stiff element of arbitrary cross section which can push an object and substantially not buckle.

Additionally in accordance with a preferred embodiment of the present invention, there is provided a coupling which couples the wire to the vibrator. The coupler includes a first shaft, the wire being fixedly attached to the first shaft, a second shaft having a longitudinal notch formed thereon at a rearward end thereof, the notch being adapted to receive a forward end of the first shaft, and a knob which turns about an outer periphery of the rearward end of the second shaft from a first radial position to a second radial position, wherein at the second radial position the knob presses the forward end of the first shaft against the notch and thereby maintain the first shaft in fixed engagement with the second shaft. Preferably a deforming apparatus is provided which imparts reciprocating motion to the second shaft.

Additionally in accordance with a preferred embodiment of the present invention, the wire moves the deformable scraper from a stowed position to an undeformed deployed position and from the undeformed deployed position to a deformed deployed position. The scraping and raking motion is substantially rearward and forward, as well as vertical.

In a preferred embodiment of the present invention, wherein the sucking is automatic, the suction device is a syringe. Preferably the syringe plunger is coupled to a motor and a biasing device which create a sucking force in the syringe.

In a preferred embodiment of the present invention, wherein the sucking is semi-automatic, the suction device is a pump.

Preferably the uterine tissue collector includes a plurality of markings adapted to indicate the penetration of the uterine tissue collector into the uterus. The markings may be ruled, or coded by different colors or different shadings.

Preferably the uterine tissue collector includes a collector adapted to collect the sucked material.

Additionally in accordance with a preferred embodiment of the present invention, the collector includes a separator and a basin, the separator diverting sucked material from the suction device to the basin.

There is also provided in accordance with a preferred embodiment of the present invention a method of collecting uterine tissue from a uterus including the steps of inserting a deformable scraper through a cervical canal into the uterus, scraping the uterus by deforming the deformable scraper and sucking scraped material into a collector.

BRIEF DESCRIPTION OF THE DRAWINGS

The present invention will be understood and appreciated more fully from the following detailed description, taken in conjunction with the drawings in which:

FIGS. 1A and 1B are respective side and top views of a uterine tissue collector constructed and operative in accordance with a preferred embodiment of the present invention;

FIG. 1C is a partial sectional illustration of the uterine tissue collector taken along lines 1C—1C in FIG. 1A;

FIG. 2 is a partial sectional side illustration of the uterine tissue collector of FIGS. 1A–1C;

FIG. 3 is a partial sectional illustration of a portion of the uterine tissue collector of FIGS. 1A–2 at a position indicated by the arrow III in FIG. 2;

FIGS. 4A and 4B are sectional illustrations of a coupling in the uterine tissue collector of FIGS. 1A–2, taken along the lines IV—IV in FIG. 3;

FIG. 6C is an illustration of the raking swath of the uterine tissue collector shown in FIGS. 1A–2;

FIGS. 7F and 7G are respective top and side view simplified illustrations of a cannula and scraper constructed and operative in accordance with yet another preferred embodiment of the present invention;

FIG. 7H is a spread out, simplified illustration of the scraper of FIGS. 7F and 7G;

FIG. 8A is a sectional illustration of the deformable scraper taken along lines VIII—VIII in FIGS. 7A and 7B;

FIG. 8B is a sectional illustration of a deformable scraper and cannula constructed and operative in accordance with another preferred embodiment of the present invention;

FIG. 9 is a partial sectional side illustration of a deformable scraper constructed and operative in accordance with another preferred embodiment of the present invention;

FIGS. 11A–11C are partial sectional top views of the deformable scraper shown in FIGS. 10A–10C in respective stowed, deployed undeformed and deployed deformed states;

FIG. 11D is an illustration of the raking swath of the deformable scraper shown in FIGS. 10A–11C;

FIGS. 12A–12B are perspective illustrations of a deformable scraper constructed and operative in accordance with another preferred embodiment of the present invention;

FIG. 14 is a side view of a uterine tissue collector constructed and operative in accordance with a further embodiment of the present invention;

FIG. 15 is a sectional frontal view of a handle used in the embodiment of FIG. 14, taken along the lines XV—XV in FIG. 14;

FIG. 22 is a simplified pictorial illustration of the disposable assembly of FIG. 18 after clamping to the housing of FIG. 19;

FIGS. 23A and 23B are simplified, partially sectional, side view illustrations of vibrating and deforming a deformable scraper disposed in a cannula of the disposable assembly of FIG. 18, before and after deformation, respectively;

FIGS. 25A and 25B are simplified top view illustrations of the deformable scraper of the disposable assembly of FIG. 18 before and after deformation, respectively;

FIGS. 26A and 26B are simplified sectional illustrations of the deformable scraper of the disposable assembly of FIG. 18 before and after deformation, respectively, FIGS. 26A and 26B being taken along lines 26A—26A in FIG. 25A, and lines 26B—26B in FIG. 25B, respectively; and FIGS. 27A and 27B are simplified sectional illustrations of a deformable scraper, constructed and operative in accordance with an alternative embodiment of the present invention, before and after deformation, respectively.

DETAILED DESCRIPTION OF A PREFERRED EMBODIMENT

Figure 5A:
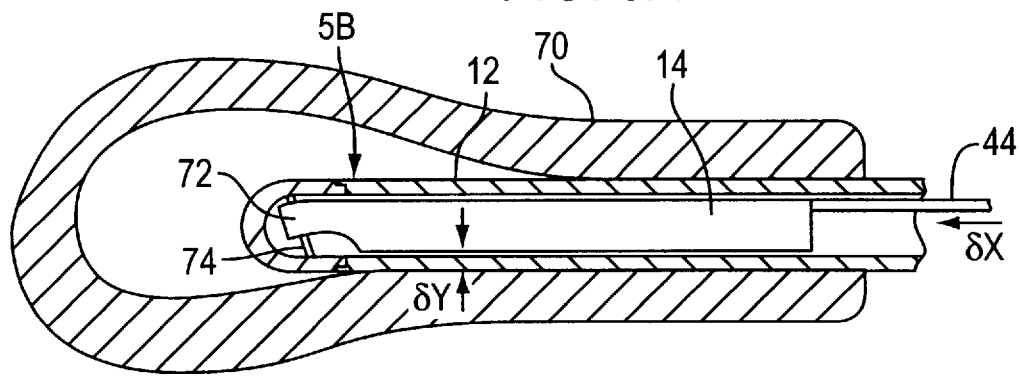
FIGS. 5A and 5B are partial sectional illustrations, respectively side and top views, of a cannula of the uterine tissue collector of FIGS. 1A–2 inserted into a uterus with the scraper of the uterine tissue collector in a deformed state.

Reference is now made to FIGS. 1A–1C and FIG. 2 which illustrate a uterine tissue collector 10 constructed and operative in accordance with a preferred embodiment of the present invention. The uterine tissue collector 10 comprises a hollow cannula 12 adapted for insertion into a uterus. The cannula 12 may be straight or bent. The cannula 12 has an aperture 9 and a deformable scraper 14 disposed at its rearward end. The operation of the scraper 14 will be described in detail further below in conjunction with FIGS. 5A–7B.

The uterine tissue collector 10 also comprises a suction device such as a syringe 16. The syringe 16 is preferably removably attached to a housing 18 by means of a clamp 20. The syringe 16 is in sealed communication with the cannula 12 via a tube 13 and a manifold 15. The housing 18 is adapted to be comfortably held in the hand of a user.

In a preferred embodiment of the present invention, the syringe 16, manifold 15, tube 13 and cannula 12 form a disposable assembly 11. After collection of uterine material and examination thereof, the assembly 11 may be discarded.

As seen clearly in FIG. 2, the housing 18 preferably comprises a motor 22 and a lead screw 26. In a preferred embodiment of the present invention, the housing 18 also includes a biasing device, preferably a spring 24. The syringe 16 includes a body collar 28 and a plunger collar 30. The body collar 28 may be fixed in a groove 32 in the housing 18. The plunger collar 30 may be held by a catch 34 which is adapted to slide axially along the lead screw 26 through a slot 27 in the housing 18.

The catch 34 comprises a tooth 38 which is adapted to engage with a thread of the lead screw 26. The catch 34 and the tooth 38 are shaped such that when the tooth 38 is engaged with one of the threads of the lead screw 26, the catch 34 is substantially held in place. Furthermore, the catch 34 and the tooth 38 are configured such that pushing the catch 34 in the direction of arrow 35 causes the tooth 38 to be slightly tilted and thus to become disengaged from the threads of the lead screw 26, thereby permitting linear motion of the catch 34 in the direction of arrow 35.

In order to create suction in the syringe 16, the plunger collar 30 is pushed in the direction of arrow 35. The pushing force disengages the tooth 38 from the threads of the lead screw 26, thereby permitting the plunger collar 30 and the catch 34 to be displaced from an extended position indicated by reference numeral 36 to a compressed position indicated by reference numeral 37. At the compressed position 37, the tooth 38 engages with one of the threads of the lead screw 26 and thereby holds the plunger of the syringe, as well as the spring 24, in a compressed position.

Activation of the motor 22 imparts rotation to the lead screw 26 via a coupling 40. Rotation of the lead screw 26 causes the tooth 38, as well as the catch 34, to move axially along the lead screw 26 in a direction opposite to arrow 35 in the same manner as a nut and screw combination. The catch 34 thus acts in a similar fashion as a ratchet.

The catch 34 may be significantly urged along its axial travel by the action of the spring 24 expanding from its contracted position. It is noted that the force imparted by the spring 24 is preferably of such strength that the motor 22 need not be capable of producing a relatively strong torque, thereby reducing the size and cost of the motor. The linear motion of the catch 34 returns the plunger head 30 towards the position 36, thereby creating a sucking force in the syringe 16. This sucking force draws material scraped by the scraper 14 into the cannula 12, the tube 13, the manifold 15 and the syringe 16.

Preferably the syringe 16 comprises a liquid for setting and preserving the tissue sample, such as formalin.

The housing 18 also comprises a deformer which deforms the scraper 14. In a preferred embodiment of the present invention, and as shown in FIG. 2, the deformer is an electromagnetic vibrator 42. The vibrator 42 is coupled to the scraper 14 by means of a wire 44 which is shown in FIGS. 2, 3, 5A, 5B, 6A and 6B.

In a preferred embodiment of the present invention, the motor 22 and the vibrator 42 are powered by a battery 23 shown in FIG. 2. Alternatively, the motor 22 and the vibrator 42 may be connected by a power cord to a mains outlet and powered via a DC converter. Preferably a switch 17, shown in FIG. 1B, is used to operate the motor 22 and the vibrator 42. Alternatively, separate switches may be provided for separate operation of the motor 22 and the vibrator 42.

In a preferred embodiment of the present invention, a display 19 is provided on the housing 18 as shown in FIG. 1A. The display 19 is preferably an LCD display and may display information such as state of the battery 23, rate of suction and/or frequency of vibration. Preferably suitable sensors sense the information as required.

Reference is now made to FIGS. 3, 4A and 4B which illustrate in detail the coupling of the vibrator 42 to the wire 44. The vibrator 42 is provided with a coupling 46 (also shown in FIG. 2). A rearward end 47 of the coupling 46 has an axial notch 48 which is adapted to receive a forward end 49 of a shaft 50. The wire 44 is embedded into a rearward end 51 of the shaft 50. As is seen clearly in FIG. 4A, the forward end 49 preferably rests in the notch 48 on a small rod 52, and the perimeter of the forward end 49 juts beyond the perimeter of the rearward end 47 of the coupling 46. Surrounding the rearward end 47 of the coupling 46 is a knob 54 provided with handles 55 and 56. The knob 54 is also preferably provided with an internal radial ridge 58 which rides inside a radial groove 60 preferably machined on the perimeter of the rearward end 47 of the coupling 46.

In order to operate the uterine tissue collector 10, a user attaches the disposable assembly 11 to the housing 18 in a manner described in the following paragraphs, such that the syringe 16 is in operable communication with the biasing device 24 and the motor 22 and the scraper 14 is in operable communication with the vibrator 42.

Operable communication between the syringe 16 and the spring 24 and the motor 22 is achieved by placing the syringe 16 on the housing 18 such that the body collar 28 is fixed in the groove 32 and the plunger collar 30 is fixed in the catch 34, as shown in FIG. 2. The user clamps the syringe to the housing 18 by means of the clamp 20.

As the user places the syringe 16 on the housing 18, the user also inserts the forward end 49 of the shaft 50 into the notch 48 of the rearward end 47 of the coupling 46. The user then turns the knob 54 in a direction indicated by arrow 62 in FIG. 4A to the position illustrated in FIG. 4B, thereby jamming the forward end 49 of the shaft 50 between the rod 52, the inner surface of the knob 54 and the notch 48 of the coupling 46, and thus securely coupling the wire 44 to the vibrator 42, and thereby placing the scraper 14 in operable communication with the vibrator 42.

Friction between the various parts retains the knob 54 in place. It is appreciated by persons skilled in the art that the coupling 46 obviates the need for exact alignment of the various moving parts.

The vibrator 42 moves the coupling 46 back and forth a distance delta X as indicated in FIG. 3. Since the coupling 46 is connected by the shaft 50 to the wire 44, the wire 44 also moves back and forth the distance delta X. The coupling 46 is guided during this reciprocating motion by means of a pin 62 fixedly attached to the housing 18 and which sits in an axial grove 64 of the coupling 46. It is noted that the pin 62 sitting in the groove 64 also prevents unwanted rotation of the rearward end 47 of the coupling 46 during rotation of the knob 54.

As seen in FIG. 3, the tube 13 communicates with the manifold 15 via an orifice 66. In order to maintain the vacuum needed for suction, a flexible bellows 68 is disposed at a forward end of the tube 13. The shaft 50 is sealably disposed through a hole in the bellows 68. As the coupling 46 vibrates back and forth, the bellows 68 deforms accordingly and substantially seals the tube 13 and the shaft 50.

In order to help prevent foreign matter from infiltrating the housing 18 at the location of the coupling 46, there is preferably provided a bellows 69 attached to the housing 18 around the coupling 46 forward of the knob 54.

Reference is now made to FIGS. 5A–7B which illustrate the action of the scraper 14 inside a uterus 70. As seen in FIGS. 5A and 5B, a rearward end 72 of the scraper 14 is slidably attached to an inclined post 74 disposed at the rearward end of the cannula 12. Normally when the cannula 12 is inserted into the uterus 70, the scraper 14 contacts the wall of the uterus 70. As the wire 44 moves linearly towards the rearward end 72, it causes the rearward end 72 of the scraper 14 to slide up the post 74, thereby moving the scraper away from the wall of the uterus 70, as seen in FIG. 5A.

Figure 5B:
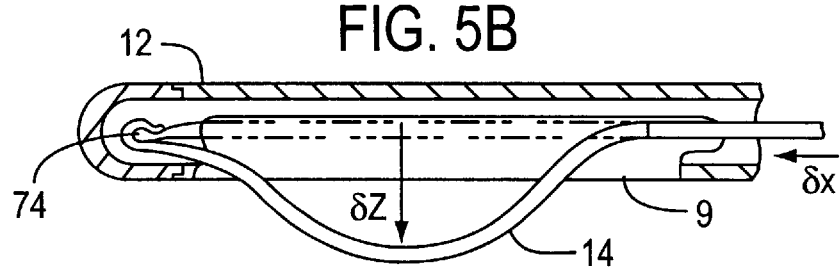

Since the scraper 14 can not slide further along the post 74, it buckles laterally outward from the central axis of the cannula 12 and through the aperture 9, as seen clearly in FIG. 5B. Thus a linear displacement delta X of the wire 44 deforms the scraper 14, thereby displacing it a distance delta Y away from the wall of the uterus 70, as seen in FIG. 5A, and a distance delta Z laterally outward from the central axis of the cannula 12, as seen in FIG. 5B.

The user then moves the uterine tissue collector 10 to bring the scraper 14 into contact with the wall of the uterus 70. Friction between the scraper 14 and the wall of the uterus 70 may help maintain the scraper 14 in the deformed configuration described above.

Figure 6A:
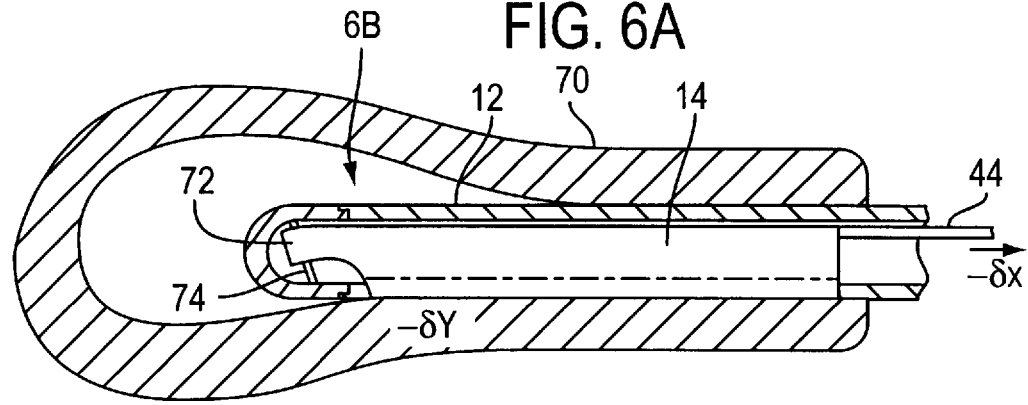
FIGS. 6A and 6B are partial sectional illustrations, respectively side and top views, of the cannula of the uterine tissue collector of FIGS. 1A–2 inserted into a uterus with the scraper of the uterine tissue collector in an undeformed state.
Figure 6B:
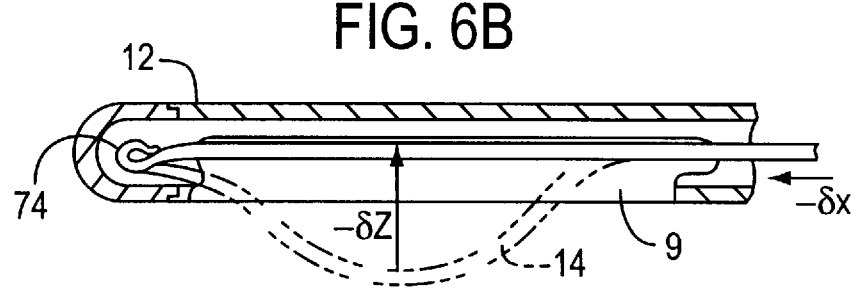
Figures 7A, 7B:
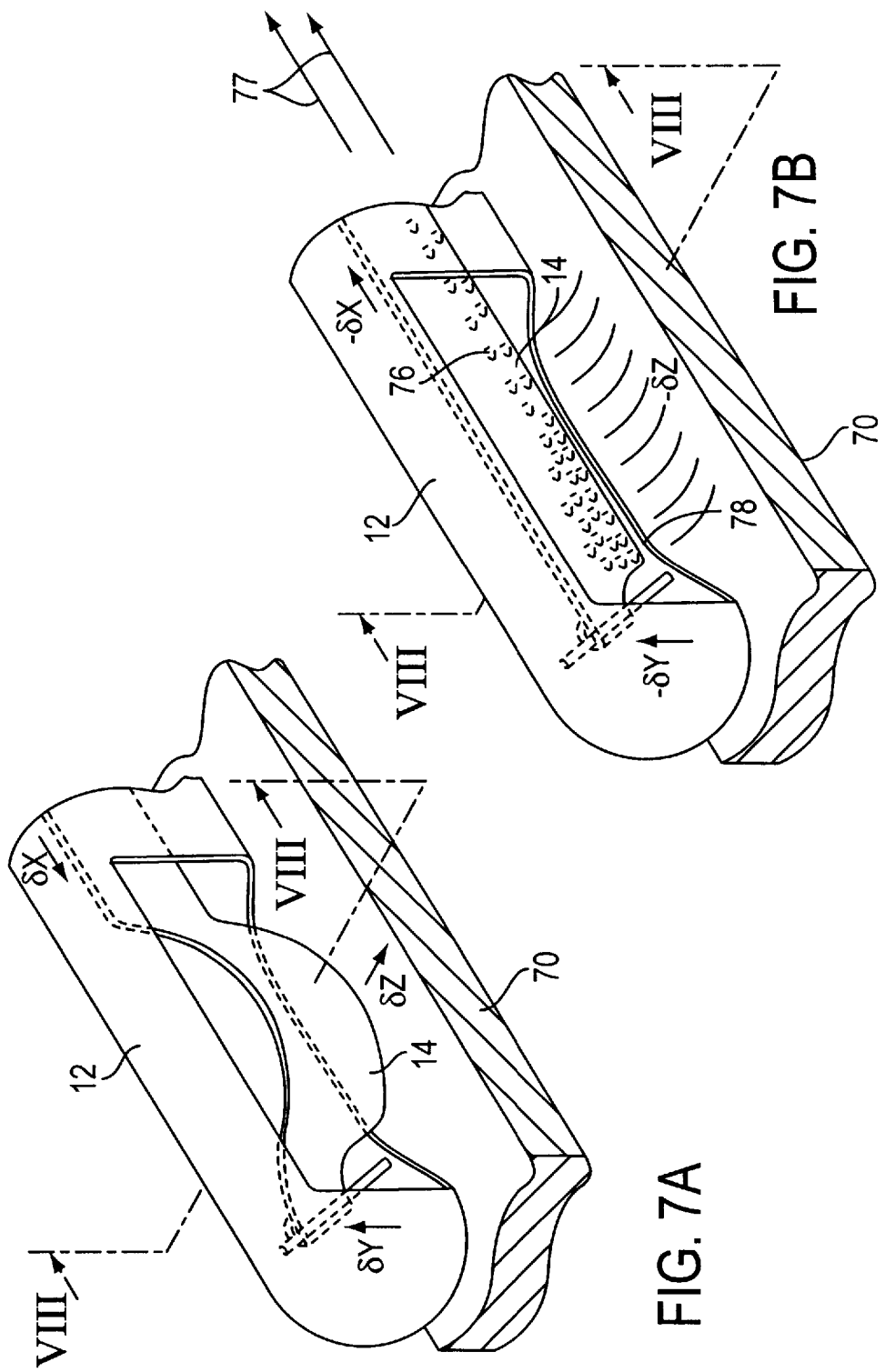
FIGS. 7A and 7B are perspective illustrations of the cannula of the uterine tissue collector of FIGS. 1A–1C, the deformable scraper being respectively deformed and undeformed.

As seen in FIGS. 6A and 6B, and in perspective in FIGS. 7A and 7B, as the wire 44 is retracted a distance delta X, the scraper 14 slides back down the post 74 a distance delta Y, and is further pressed against the wall of the uterus 70 and returns a distance delta Z to its original undeformed shape. As the scraper returns the distance delta Z, it scrapes and rakes uterine material 76 from the uterus 70. The uterine material 76 is sucked and plucked by the syringe 16 in the direction indicated by arrows 77.

It is a particular feature of the present invention that the cross-sectional shape of the cannula 12 is rectangular at its rearward end, as seen in FIG. 8A, except for a rounded tip. The rectangular shape ensures that the entire width of the scraper 14 can easily protrude laterally from the cannula 12.

In addition to the scraping and raking action of the scraper 14 against the uterus, it is a particular feature of the present invention that additional uterine material, such as a growth which protrudes from the uterine wall, may be gathered by the action of the bottom edge of the scraper 14 against an edge 78 of the cannula 12. As seen in FIG. 8B, this feature may be augmented by beveling the edge 78 so that it is operable as a blade. As the scraper 14 returns towards the central axis of the cannula 12, it passes over the beveled edge 78 and acts like a scissors which can snip a protrusion 80 of uterine material.

Reference is now made to FIG. 6C which illustrates the raking swath of the uterine tissue collector shown in FIGS. 1A–2. The scraping and raking motion is substantially lateral and medial in the swath designated by numeral 73. After scraping and raking the swath 73, the cannula 12 is positioned rearward or forward in another region of the uterus and scraping and raking is repeated. The process is repeated until the desired area has been scraped and raked. Preferably graduations 75 are provided to help inform the user of the level of penetration of the cannula 12. The graduations 75 may be in the form of ruled markings as shown in FIG. 6C. Alternatively, or additionally, the graduations 75 may be different colored markings or differently shaded markings.

Figure 7D:
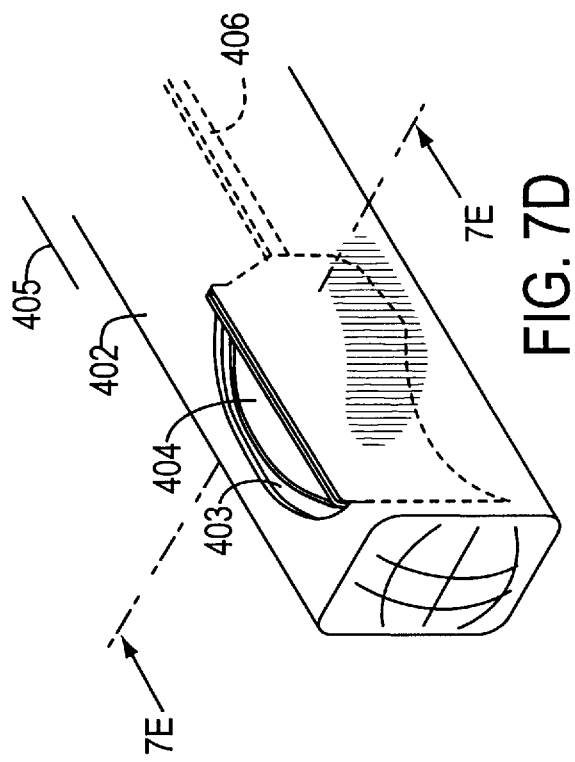
FIGS. 7C and 7D are partial perspective illustrations of a cannula and a deformable scraper of a uterine tissue collector constructed and operative in accordance with another preferred embodiment of the present invention, the deformable scraper being respectively undeformed and deformed.
Figure 7C:
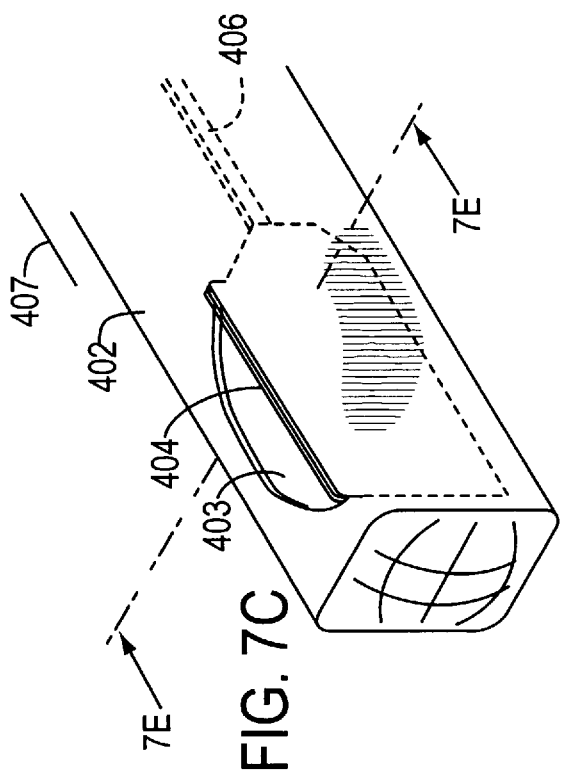
Figure 7E:
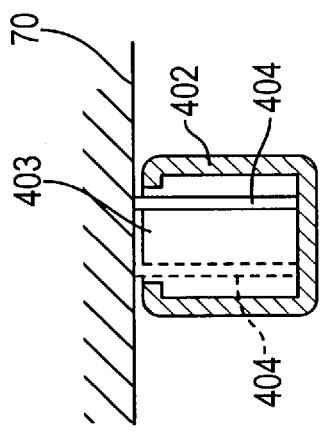
FIG. 7E is a sectional illustration of the deformable scraper and cannula of the embodiment of FIGS. 7C and 7D, taken along lines 7E—7E in FIGS. 7C and 7D.

Reference is now made to FIGS. 7C–7E which illustrate a cannula and a scraper constructed and operative in accordance with another preferred embodiment of the present invention. A cannula 402 has a substantially rectangular shape at a rearward end thereof, and has substantially the same configuration as the cannula 12 shown and described above with reference to FIGS. 1A–7B. The cannula 402 has an aperture 403 on one face thereof, adapted to be in contact with the wall of the uterus 70, as shown in FIG. 7E.

A deformable scraper 404 is disposed in the cannula 402 and flexibly attached towards a rearward end thereof. The scraper 404 protrudes slightly through the aperture 403 in a direction upwards as viewed in FIGS. 7C–7E. This is the direction towards the wall of the uterus 70.

A wire 406 is attached to a forward end of the scraper 404. By comparing FIGS. 7C and 7D, it is appreciated that movement of the wire 406 towards the rearward end of the cannula 402, in the direction of arrow 405, causes the scraper 404 to buckle laterally. Conversely, movement of the wire 406 towards the forward end of the cannula 402, in the direction of arrow 407 which is substantially opposite to the direction of arrow 405, causes the scraper 404 to straighten, as similarly described hereinabove for the embodiment of FIGS. 1A–7B. The scraper 404 scrapes uterine material when pressed against the uterine wall.

It is noted that the aperture 403 is on only one face of the cannula 402 of the embodiment of FIGS. 7C–7E, whereas the aperture 9 extends to an additional face of the cannula 12 of the embodiment of FIGS. 1A–7B. The relatively smaller aperture 403 leads to greater suction which is particularly useful in plucking and collecting small uterine material.

Reference is now made to FIGS. 7F–7H which illustrate a cannula and a scraper constructed and operative in accordance with yet another preferred embodiment of the present invention. A cannula 502 has a substantially rectangular shape at a rearward end thereof, and has substantially the same configuration as the cannula 12 shown and described above with reference to FIGS. 1A–7B. The cannula 502 has an aperture 504 which gradually becomes radially deeper in a direction away from the rearward tip of cannula 502, as seen in FIG. 7G.

As seen in FIG. 7F, aperture 504 has a main portion 506 and an elongate narrow portion 508.

Disposed in cannula 502 is a deformable scraper 510 which is somewhat shaped like an elongated letter U, as seen in FIG. 7F. An end 512 of scraper 510 is fixedly attached to a wire 514, and an opposite end 516 of scraper 510 is fixedly attached to an inner wall of cannula 502. The free moving leg of the U-shaped scraper 510, designated by reference numeral 518, may be used to scrape and rake a uterus. Part of leg 518, towards end 512 of scraper 510, is disposed in narrow portion 508 of aperture 504, as seen in FIG. 7F.

As seen in FIG. 7H, which illustrates scraper 510 spread out, scraper 510 has an arcuate protrusion 520 along leg 518.

Wire 514 is attached to a vibrator (not shown) which causes wire 514 and scraper 510 to oscillate generally in the direction of arrows 522 and 524, shown in FIG. 7F. It is appreciated that when scraper 510 is pressed against a uterus and is caused to oscillate generally in the direction of arrows 522 and 524, scraper 510 scrapes and rakes uterine material from the uterus.

If it is desired to cut uterine material, the amplitude of oscillation may be increased such that scraper 510 passes underneath a region of aperture 504, designated by reference numeral 526. The scissors-like action of the U-shaped scraper 510 scraping against the upper inner wall of cannula 502 at region 526 helps in cutting uterine material. The arcuate protrusion 520 of scraper 510 also helps gather in uterine material.

It is appreciated that a variety of couplings and deformers may be used in different embodiments of the present invention to operate the scraper 14. One such embodiment is shown in FIG. 9 wherein a bent wire 84 is attached to the scraper 14 at a junction 85 which is preferably off-center to the scraper 14. As the wire 84 moves linearly a distance delta X in the direction indicated by arrow 86, the scraper 14 is displaced and deformed as described hereinabove in conjunction with FIGS. 5A–7B. As the wire 84 moves further linearly in the direction indicated by arrow 86, it causes the junction 85 to be rotated in the direction of arrow 87, thereby thrusting the scraper against the uterine wall. This augments the raking and scraping motion.

Reference is now made to FIGS. 10A–10C and FIGS. 11A–11C which respectively illustrate side and top views of another scraper constructed and operative in accordance with a preferred embodiment of the present invention. A deformable scraper 114 is disposed inside a hollow cannula 112. Attached to a rearward end 116 of the scraper 114 is a prod wire 118, whose forward end 120 is adapted to slide axially in a channel 122 on the inner wall of the cannula 112. Attached to a forward end of the scraper 114 is a wire 144 whose forward end is coupled with a deformer as described hereinabove in conjunction with FIG. 3. The material of the scraper 114 is more flexible than the material of the prod wire 118.

Figure 10A:
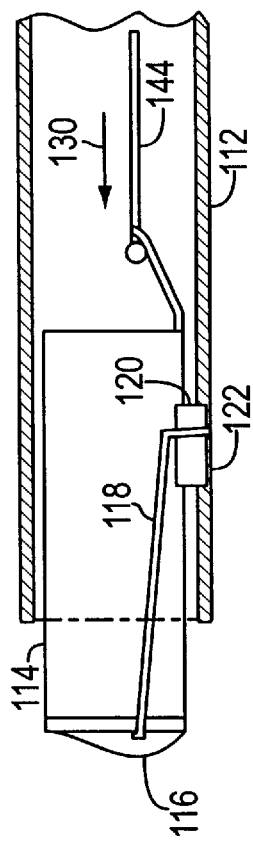
FIGS. 10A–10C are partial sectional side views of a deformable scraper constructed and operative in accordance with yet another preferred embodiment of the present invention in respective stowed, deployed undeformed and deployed deformed states.
Figure 10B:
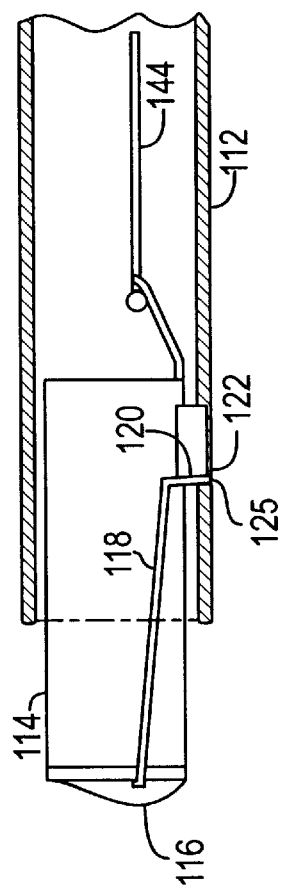
Figure 10C:
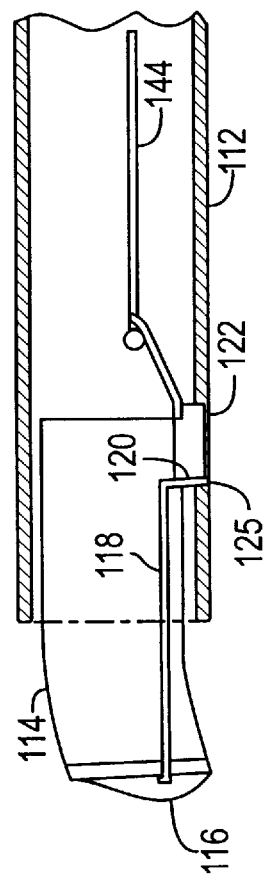

Reference is now made to FIGS. 10A and 11A which show an initial state in which the forward end 120 of the prod wire 118 is situated near the forward end of the channel 122. As the wire 144 moves linearly towards the rearward end of the channel 122 in the direction indicated by arrow 130, the forward end 120 of the prod wire 118 is shifted to and butts against the rearward end of the channel 122, here indicated by reference numeral 125 in FIGS. 10B and 11B. The linear motion of the wire 144 simultaneously deploys the scraper 114 by moving it out of the cannula 112. It is noted that the scraper 114 is still in an undeformed configuration in FIGS. 10B and 11B. Further pushing of the wire 144 in the direction 130, as shown in FIGS. 10C and 11C, causes the rearward end 116 of the scraper 114 to deform and bulge outward as shown in FIG. 11C, as well as to deflect vertically as shown in FIG. 10C. This deformation is due to the fact that the rearward end 116 of the scraper 114 is attached to the prod wire 118 and the forward end 120 of the prod wire 118 is prevented from further linear motion in the direction 130 by being butted against the rearward end of the channel 122.

Retraction of the wire 144 in a direction opposite to 130 returns the scraper 114 to its original undeformed state. As the scraper 114 retracts into the cannula 112, it scrapes against the uterus and collects uterine material. The uterine material is then sucked and plucked by a suction device as described hereinabove.

Reference is now made to FIG. 11D which illustrates the raking swath of the deformable scraper shown in FIGS. 10A–11C. The scraping and raking motion is substantially rearward and forward in the swath designated by numeral 138. It is noted that the swath 138 is wider than the width of the cannula 112. After scraping and raking the swath 138, the cannula 112 is repositioned in another region of the uterus and scraping and raking is repeated. The process is repeated until the desired area has been scraped and raked. Preferably graduations 139 are provided to help inform the user of the level of penetration of the cannula 112. The graduations 139 may be in the form of ruled markings as shown in FIG. 11D. Alternatively, or additionally, the graduations 139 may be different colored markings or differently shaded markings.

Reference is now made to FIGS. 12A–12B which illustrate a scraper 180 constructed and operative in accordance with another preferred embodiment of the present invention. The scraper 180 is housed in a cannula 182. The scraper 180 is stowed in the cannula 182 in a compressed position as shown in FIG. 12A. As the scraper 180 is deployed by being moved rearward out of the cannula 182, it springs outward to a larger uncompressed shape as shown in FIG. 12B. The scraper 180 is preferably constructed of a flexible, resilient material such that the scraper 180 may bulge outward while remaining relatively stiff in the vertical direction.

Figure 13A:
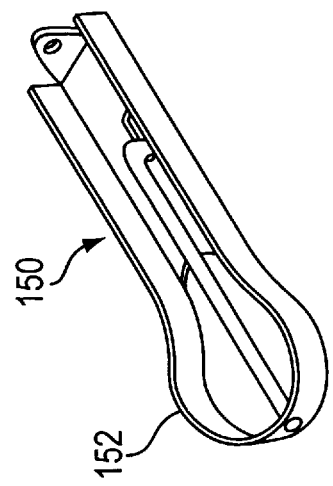
FIGS. 13A–13C are perspective illustrations of three different deformable scrapers constructed and operative in accordance with a preferred embodiment of the present invention.

It is appreciated that different embodiments of the scraper 114 illustrated in FIGS. 10A–12B may be constructed to improve or vary its scraping and/or cutting capability. FIG. 13A illustrates a scraper 150 similar in construction and operation to the embodiment described in FIGS. 10A–11C. Scraping surfaces 152 may be sharpened to enhance cutting capability.

Figure 13B:
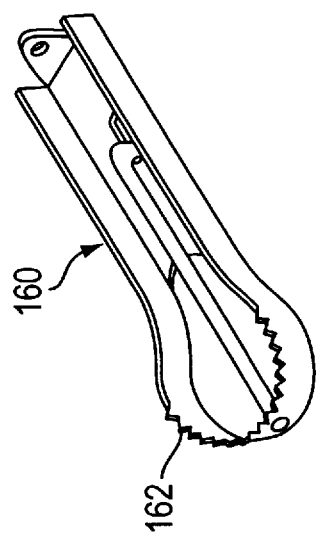

FIG. 13B illustrates a scraper 160 which has serrated edges 162 for enhanced scraping capability.

Figure 13C:
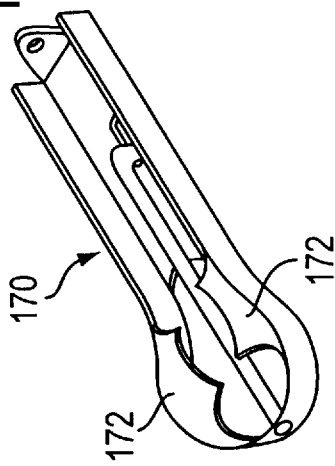

FIG. 13C illustrates a scraper 170 which has scissor edges 172. As the scraper 170 deforms, the scissor edges 172 move towards one another and thus can cut tissue as well as scrape.

The preferred embodiments of the present invention described hereinabove scrape and suck automatically. After uterine material has been sucked, the assembly comprising the tube 13, the manifold 15 and the syringe 16 is detached from the housing 18 by releasing clamp 20 and turning knob 54 to release the shaft 50. The sucked uterine material, which may be found either on the scraper 14 or in the cannula 12, the tube 13, the manifold 15 or the syringe 16, and which has been preferably fixed with a fixing solution such as formalin, is then removed for examination.

Figure 16:
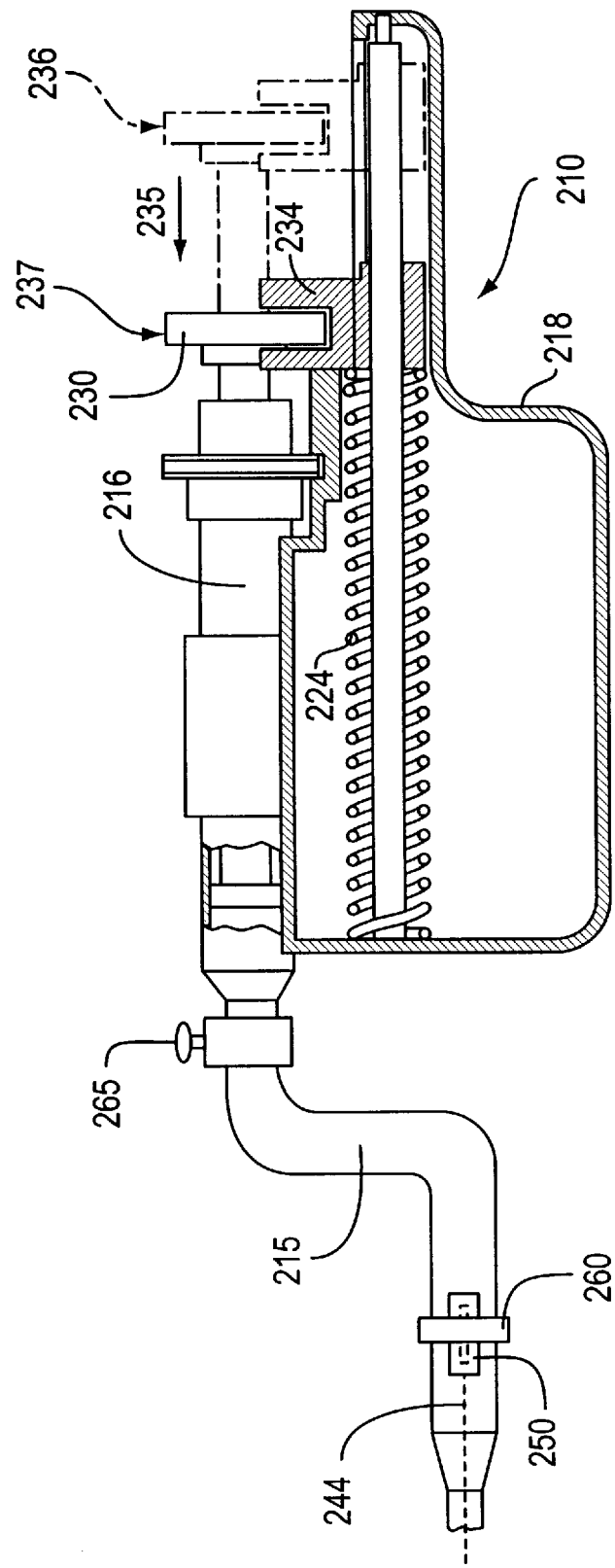
FIG. 16 is a partial sectional side view of the embodiment of FIG. 14.

Reference is now made to FIGS. 14–16 which illustrate a uterine tissue collector 210, constructed and operative in accordance with another embodiment of the present invention, which scrapes manually and sucks automatically. The uterine tissue collector 210 preferably comprises a housing 218, a cannula 212 and a deformable scraper 214 disposed at a rearward end thereof. A forward end of the cannula 212 is preferably in sealed fluid communication with a tube 213 which is preferably in sealed fluid communication with a manifold 215. The manifold 215 is preferably in sealed fluid communication with a suction device, such as a syringe 216, via a valve 265.

The syringe 216 preferably includes a plunger collar 230 which is in engagement with a catch 234. Inside the housing 218 is preferably disposed a biasing device, such as a spring 224, which is in operative engagement with the catch 234, as seen in FIG. 16.

In order to create suction in the syringe 216, the plunger collar 230 is pushed in the direction of arrow 235 from an extended position indicated by reference numeral 236 to a compressed position indicated by reference numeral 237, as shown in FIG. 16, thereby compressing the spring 224. The valve 265 is then closed, thereby creating a vacuum which maintains the plunger of the syringe 216 and the spring 224 in a compressed position. The valve 265 is then slowly opened and the spring 224 returns to an extended position, thereby pushing the plunger collar 230 towards the extended position 236 and creating a sucking force in the syringe 216. This sucking force draws material scraped by the scraper 214 into the cannula 212, the tube 213, the manifold 215 and the syringe 216. The opening of the valve 265 is used to control the sucking force.

Preferably the syringe 216 contains a liquid for setting and preserving the tissue sample, such as formalin.

The housing 218 also comprises a deformer which deforms the scraper 214. In a preferred embodiment of the invention, the deformer is a wire 244 which is attached to the scraper 214 at one end thereof. The wire 244 is preferably attached at an opposite end thereof to a handle 260 located along the manifold 215. Preferably the handle 260 sealably passes through a grommet 250 into the manifold 215 as shown in FIG. 15.

In order to deploy the scraper 214, the handle 260 is used to push the wire 244 in a direction indicated by arrow 262, thereby pushing on the scraper 214 which exits the cannula 212 and deforms and bulges outwards, substantially as described hereinabove for the embodiment of FIGS. 10A–11C. A user then may manually scrape and rake a uterus with the scraper 214.

Figure 17:
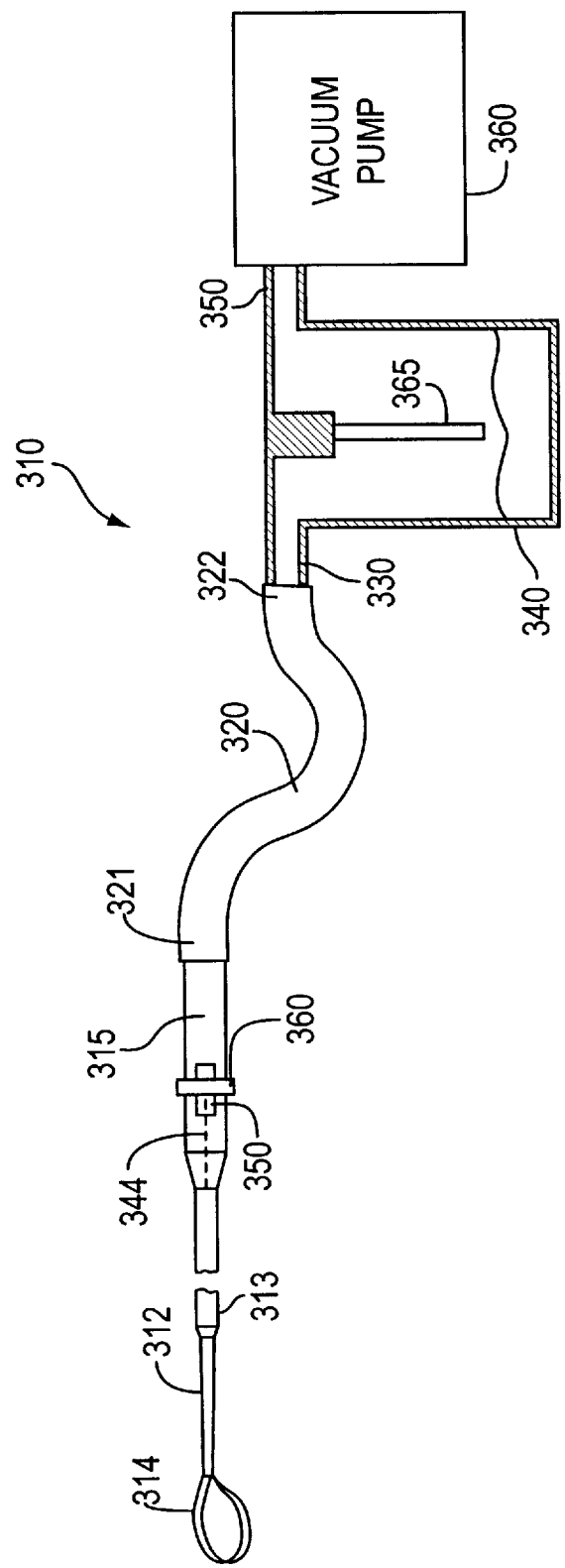
FIG. 17 is a simplified illustration of a side view of another uterine tissue collector constructed and operative in accordance with a preferred embodiment of the present invention.

Reference is now made to FIG. 17 which illustrates a uterine tissue collector 310 constructed and operative in accordance with another embodiment of the present invention which scrapes manually and sucks semi-automatically. The construction of the uterine tissue collector 310 is substantially the same as that of the uterine tissue collector 210 described hereinabove. The uterine tissue collector 310 comprises a cannula 312 and a scraper 314 disposed at an end thereof. The collector 310 also preferably comprises a tube 313, a wire 344, a manifold 315, a handle 360 and a grommet 350, all of which are substantially identical to the tube 213, the wire 244, the manifold 215, the handle 260 and the grommet 250 respectively, of the embodiment of FIGS. 14–16.

The uterine tissue collector 310 differs from the uterine tissue collector 210 described hereinabove in the type of suction. The suction device in the uterine tissue collector 310 is a vacuum pump 360.

The operation of uterine tissue collector 310 and vacuum pump 360 is now described. As seen in FIG. 17, a rearward end 321 of a flexible tube 320 is preferably in sealed fluid communication with manifold 315. A forward end 322 of the tube 320 is in sealed fluid communication with a rearward connector 330 of a basin 340. The basin 340 is preferably provided with a forward connector 350 which is preferably in sealed fluid communication with the vacuum pump 360. The vacuum pump 360 sucks uterine material scraped by the scraper 314 through the tube 313, manifold 315 and flexible tube 320 into the basin 340 via the rearward connector 330. Disposed in the basin 340 is a separator 365 which diverts material sucked through the rearward connector 330 towards the bottom of the basin 340 where the material collects. The basin 340 is detached to remove the collected material for examination.

Reference is now made to FIGS. 18–22 which illustrate a uterine tissue collector 600 constructed and operative in accordance with yet another preferred embodiment of the present invention.

Figure 18:
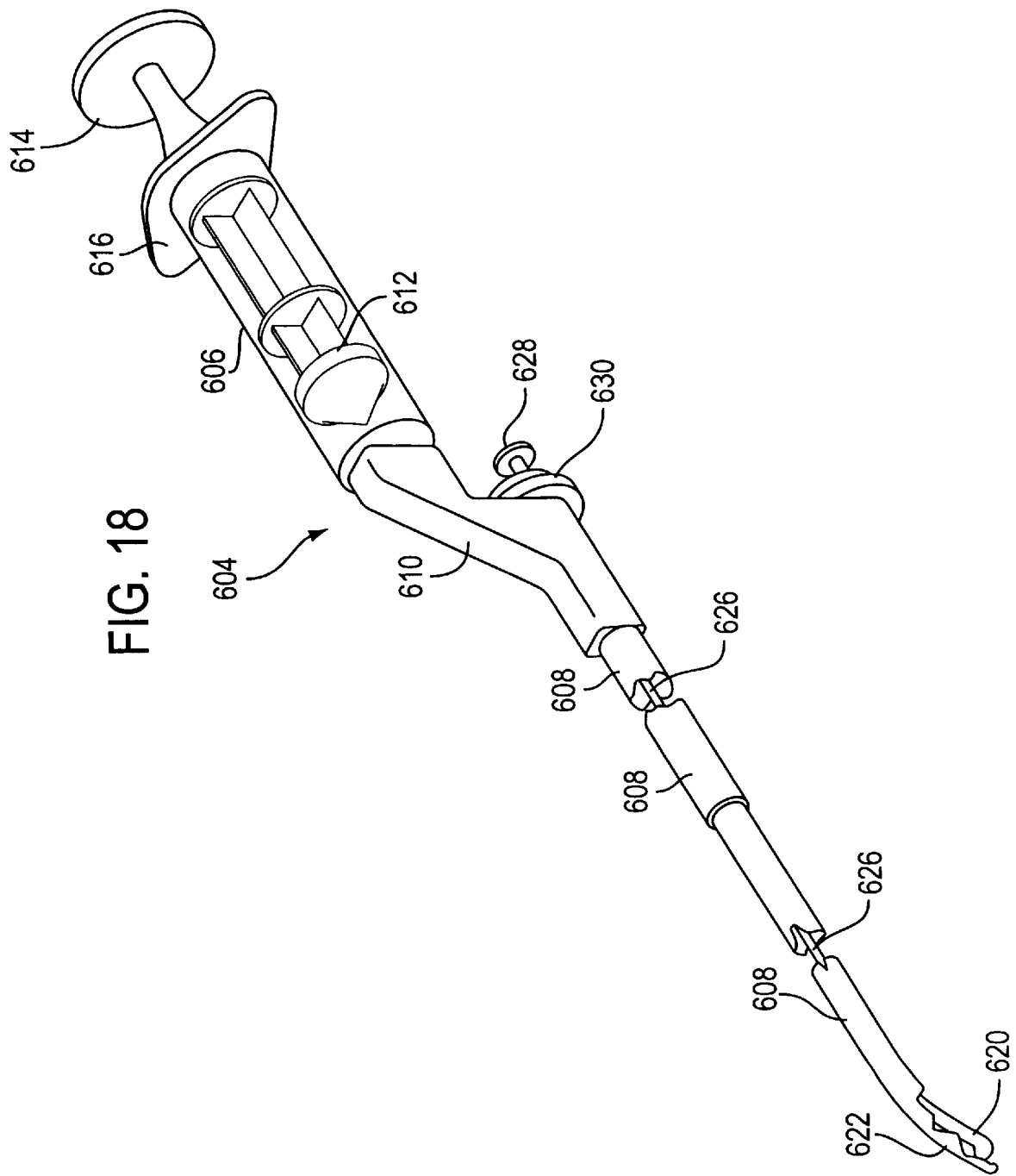
FIG. 18 is a simplified pictorial illustration of a disposable assembly used with a uterine tissue collector constructed and operative in accordance with yet another preferred embodiment of the present invention.

As seen in FIG. 18, uterine tissue collector 600 includes a housing 602 and a disposable assembly 604. Referring particularly to FIG. 18, disposable assembly 604 preferably includes a syringe 606 which is in fluid communication with a cannula 608 via a manifold 610. Syringe 606 preferably includes a plunger 612, a plunger collar 614, and a body collar 616. A deformable scraper 620 is disposed at a distal end 622 of cannula 608. Scraper 620 is attached to a wire 626 which is connected to a wire coupling 628 via a diaphragm 630. Diaphragm 630 substantially seals cannula 608 and manifold 610.

Figure 19:
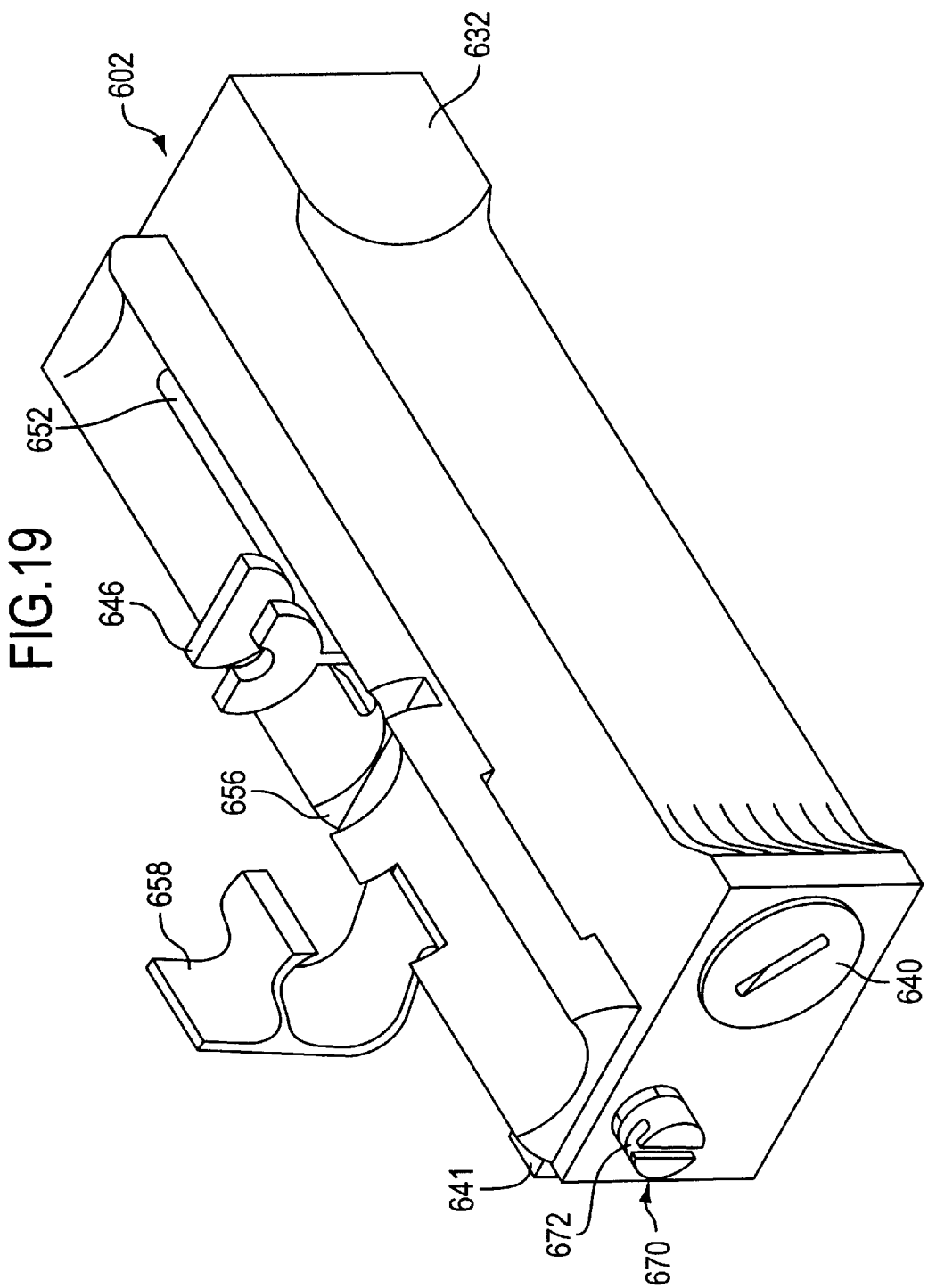
FIG. 19 is a simplified pictorial illustration of a housing to which attaches the disposable assembly of FIG. 18.
Figure 21:
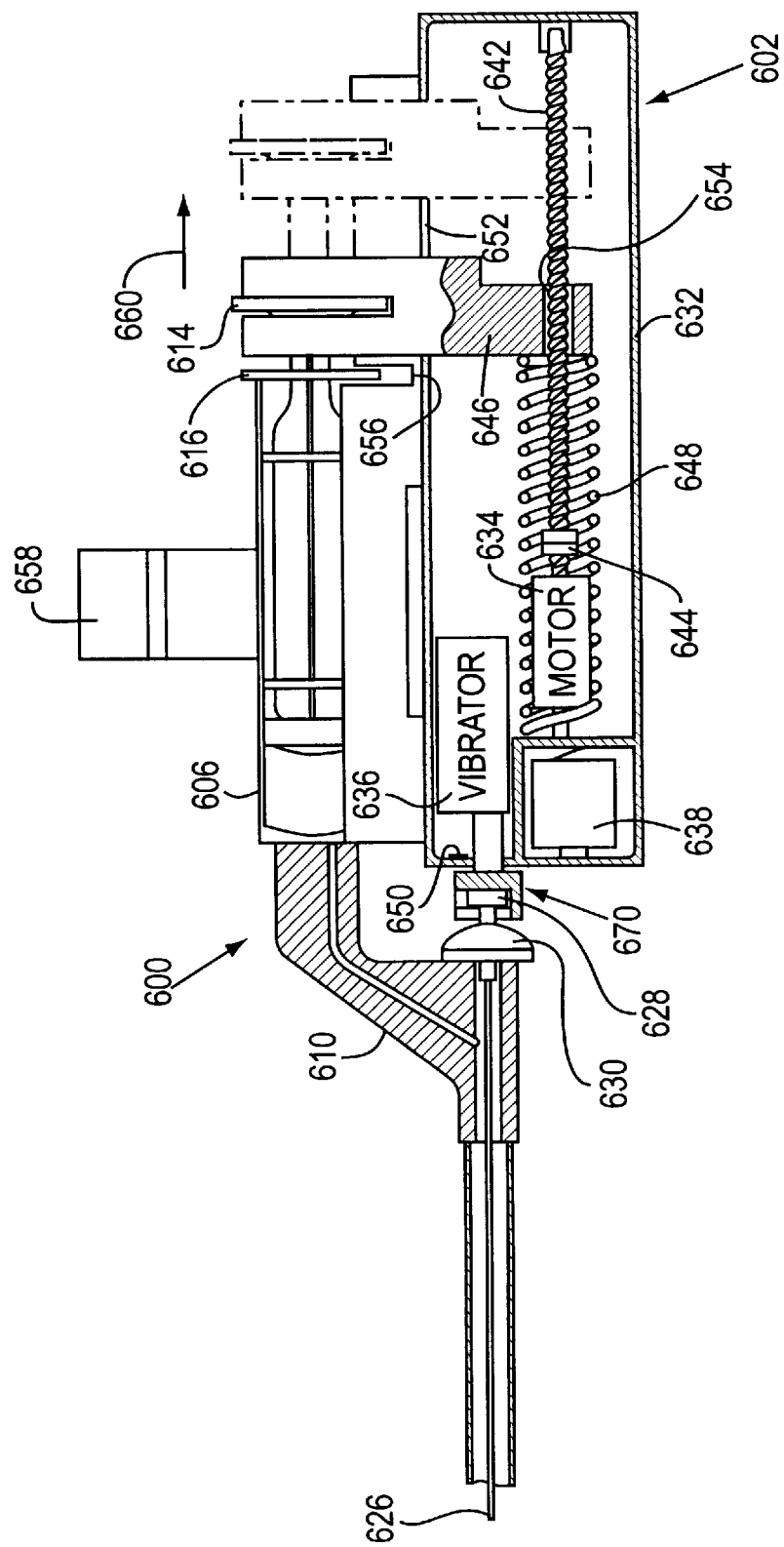

Referring to FIG. 21, it is seen that housing 602 preferably includes a hand-held portion 632 which houses a motor 634, a vibrator 636 and a battery 638. Battery 638 may be inserted in and removed from housing 602 via a battery compartment cover 640 (FIG. 19). Preferably a switch 641 is provided for operating both motor 634 and vibrator 636.

Referring again to FIG. 21, it is seen that motor 634 preferably rotates a lead screw 642 via a coupling 644. A catch 646 is preferably threadably engaged with lead screw 642, and a tensioning device, such as a spring 648, is preferably tensioned between an inner wall 650 of housing 602 and catch 646. Catch 646 preferably protrudes into housing 602 via a slot 652 and engages lead screw 642 by means of a tooth 654.

Housing 602 also preferably has a groove 656 in which may be inserted body collar 616 of syringe 606. Syringe 606 may be clamped to housing 602 by means of a clamp 658.

Suction may be created in syringe 606 by the combined action of motor 634 rotating lead screw 642 and spring 648 pushing against catch 646, thereby causing plunger collar 614 to be moved in a direction indicated by an arrow 660, as shown in FIG. 21. The creation of suction is substantially as described for uterine tissue collector 10, with reference to FIG. 2.

As seen in FIG. 21, vibrator 636 is preferably connected to a vibrator coupling 670. Vibrator coupling 670 has a generally T-shaped notch 672, as seen further in FIG. 19.

Figure 20:
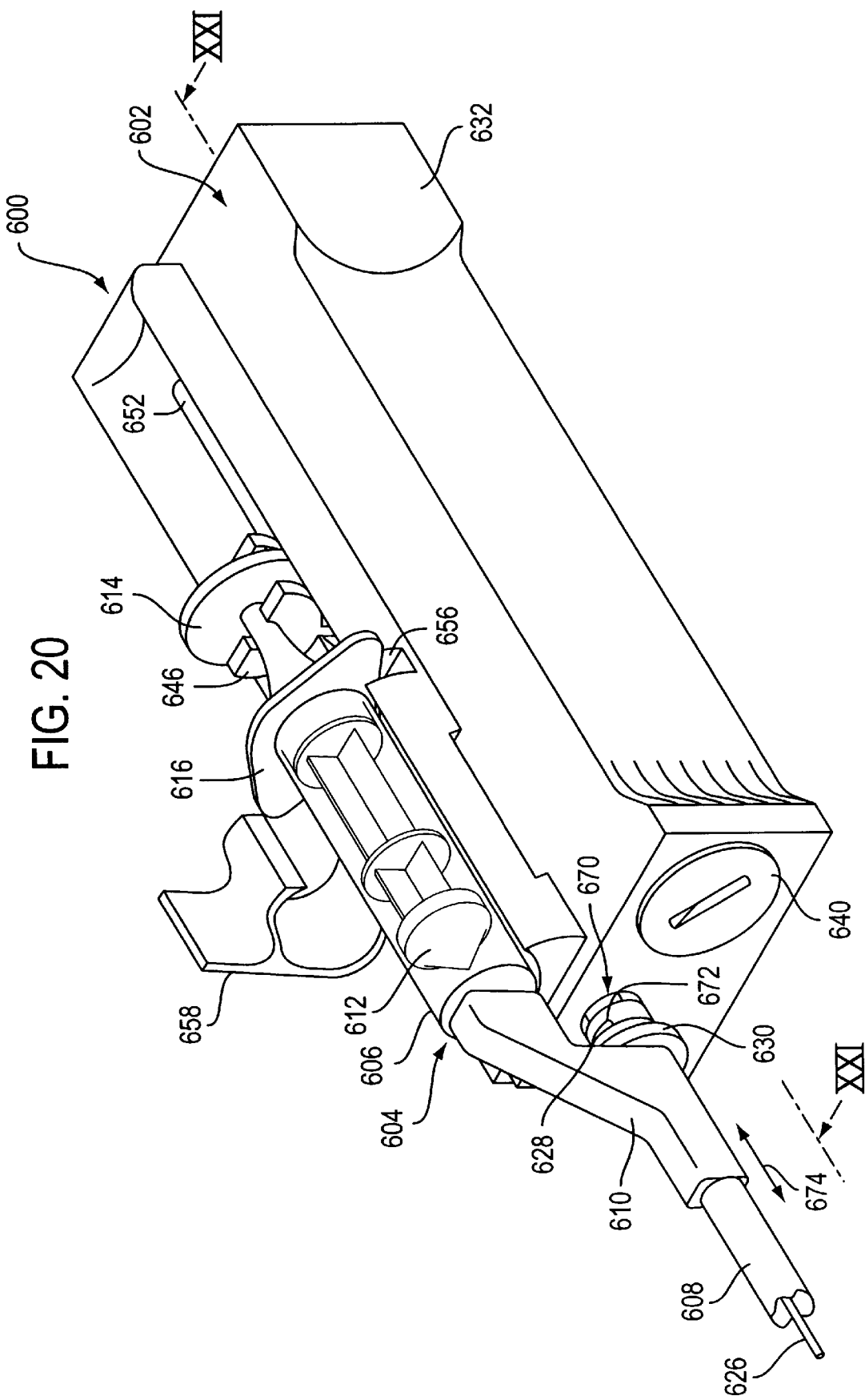
FIGS. 20 and 21 are simplified pictorial and sectional illustrations, respectively, of the disposable assembly of FIG. 18 about to be clamped to the housing of FIG. 19, FIG. 21 being taken along lines XXI—XXI in FIG. 20.

Reference is now made to FIGS. 20 and 22. It is seen that disposable assembly 604 may be attached to housing 602 by placing wire coupling 628 into notch 672 of vibrator coupling 670, body collar 616 into groove 656, and plunger collar 614 into catch 646. Vibrator coupling 670 preferably is free to move along an axis 674, thereby allowing easy alignment of wire coupling 628 with notch 672. As seen in FIG. 22, clamp 658 may be used to clamp syringe 606 to housing 602.

Reference is now made to FIGS. 23A and 23B which illustrate the vibratory action of vibrator 636. As vibrator 636 vibrates in a generally linear, back-and-forth motion along axis 674, vibrator coupling 670 imparts substantially the same motion to wire coupling 628 and wire 626. In FIG. 23A, wire 626 is shown pulled towards housing 602 and scraper 620 is not deformed. In FIG. 23B, wire 626 is shown pushed away from housing 602 and scraper 620 is deformed. As seen in FIG. 23B, diaphragm 630 contracts to substantially a fluid seal in manifold 610 and cannula 608. The nature of the deformation of scraper 620 will now be described with reference to FIGS. 24–26B.

Figure 24:
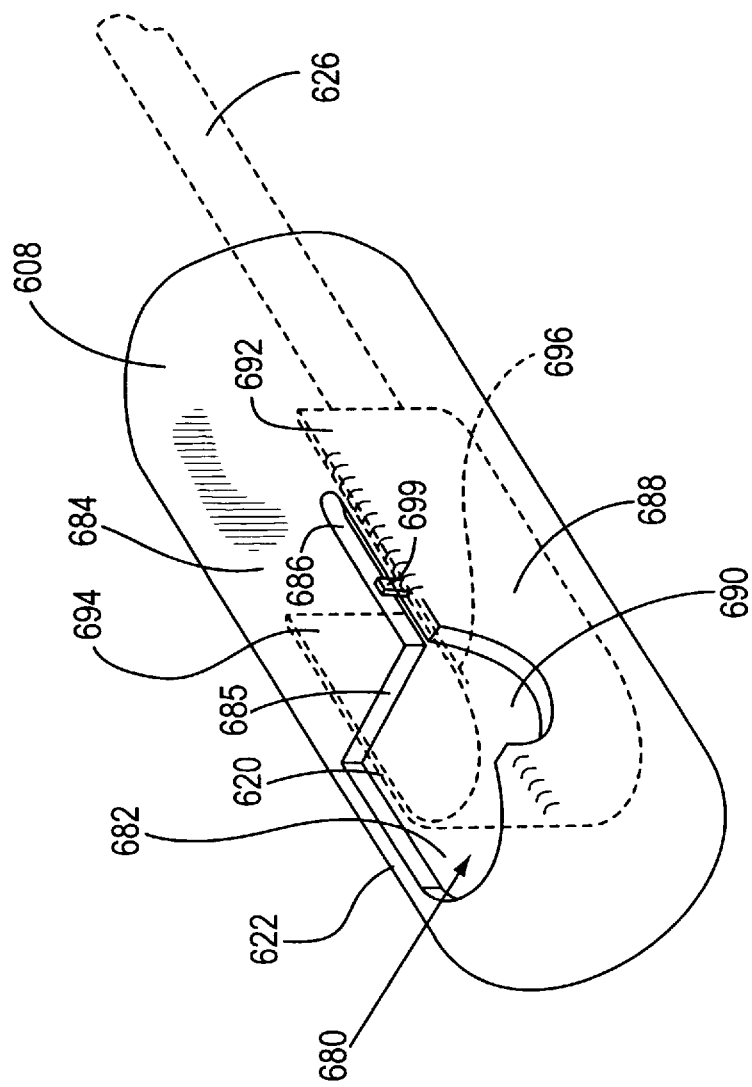
FIG. 24 is a simplified pictorial illustration of a portion of the deformable scraper shown in FIG. 18.

Referring to FIG. 24, it is seen that the cross section of distal end 622 of cannula 608 is preferably generally rectangular. Distal end 622 is preferably formed with an aperture 680 which has a generally D-shaped opening 682 on a tissue-facing surface 684 of distal end 622. D-shaped opening 682 has a generally flat edge 685 on tissue-facing surface 684. Aperture 680 continues on surface 684 as a relatively narrow, slotted portion 686, and continues on another surface 688 of distal end 622 as a generally semi-circular portion 690. Surface 688 is generally perpendicular to tissue-facing surface 684.

Deformable scraper 620 is preferably shaped in a similar fashion as deformable scraper 510, described hereinabove with reference to FIGS. 7F–7H. An end 692 of scraper 620 is fixedly attached to wire 626, and an opposite end 694 of scraper 620 is fixedly attached to an inner wall of cannula 608. The free moving leg of U-shaped scraper 620, designated by reference numeral 696, may be used to scrape and rake a uterus. Preferably a tab 699, attached to leg 696, slides in narrow, slotted portion 686 of aperture 680, as seen in FIG. 24.

Reference is now made to FIGS. 25A–26B. In FIGS. 25A and 26A, scraper 620 is not deformed. When vibrator 636 (not shown in FIGS. 25A–26B) pulls wire 626 in the direction of an arrow 697, as shown in FIGS. 25B and 26B, scraper 620 is deformed and retracts towards flat edge 685. As seen in FIG. 26B, scraper 620 may be pulled in the direction of arrow 697 such that it retracts underneath edge 685, thereby providing a scissors-type of cutting action. Thus, scraper 620 is particularly useful as a therapeutic tool for cutting tissue, such as growths, from the uterine wall.

Reference is now made to FIGS. 27A and 27B which illustrate a deformable scraper 700 of the present invention which may be disposed in cannula 608 in a similar fashion as scraper 620. Unlike scraper 620, scraper 700 preferably has an arcuate portion 702.

Scraper 700 may be deformed and retracted in the direction of arrow 697, as shown in FIG. 27B. Unlike scraper 620 which may be retracted underneath edge 685, scraper 700 may be retracted towards and against edge 685, but not underneath edge 685. As scraper 700 is retracted towards edge 685, uterine material is scraped and sucked into cannula 608. Arcuate portion 702 may provide an additional opening through which uterine material may be scraped and sucked into cannula 608. Scraper 700 is particularly useful as a diagnostic tool for collecting uterine material.

It will be appreciated by persons skilled in the art that the present invention is not limited by what has been particularly shown and described hereinabove. Rather the scope of the present invention is defined only by the claims which follow:

We claim:

1. A uterine tissue collector comprising:
    a deformable scraper which is capable of being deformed from an undeformed configuration to a deformed configuration and which scrapes a uterus while moving between said undeformed configuration and said deformed configuration;
    a deformer which deforms said deformable scraper; and
    a suction device which sucks material scraped by said deformable scraper.

2. Apparatus according to claim 1 and also comprising a cannula having an aperture, said deformable scraper being disposed in said cannula, such that when said scraper is deformed it protrudes through said aperture and scrapes said uterus.

3. Apparatus according to claim 2 and wherein said cannula has a substantially rectangular shape towards a rearward end thereof.

4. Apparatus according to claim 2 and wherein said aperture is on one face of a rearward end of said cannula, said face being adapted to be in contact with said uterus.

5. Apparatus according to claim 4 and wherein said aperture is open on an additional face of said cannula, such that said scraper may protrude through said additional face.

6. A uterine tissue collector according to claim 1
    and wherein said deformable scraper is slidably attached to an inclined post, such that said scraper is in said deformed configuration at a first end of said inclined post and is in said undeformed configuration at a second end of said inclined post.

7. Apparatus according to claim 1, and wherein said deformable scraper scrapes in a substantially lateral and medial motion.

8. Apparatus according to claim 1, and wherein said deformable scraper has a serrated edge.

9. Apparatus according to claim 2, and wherein said cannula has a beveled edge which cuts tissue.

10. Apparatus according to claim 1, and wherein said deformable scraper deforms from a compressed configuration to a non-compressed configuration.

11. Apparatus according to claim 1, and wherein said deformable scraper cuts tissue.

12. Apparatus according to claim 2, and wherein said aperture is radially deeper in a direction away from a rearward tip of said cannula.

13. Apparatus according to claim 1, and wherein said scraper is generally U-shaped.

14. Apparatus according to claim 1, and wherein said scraper has an arcuate protrusion.

15. Apparatus according to claim 1, and wherein said deformer comprises a wire coupled to said deformable scraper.

16. Apparatus according to claim 15 and further comprising:
    a first shaft, said wire being fixedly attached to said first shaft;
    a second shaft having a longitudinal notch formed thereon at a rearward end thereof, said notch being adapted to receive a forward end of said first shaft; and
    a knob which turns about an outer periphery of said rearward end of said second shaft from a first radial position to a second radial position, wherein at said second radial position said knob presses said forward end of said first shaft against said notch and thereby maintain said first shaft in fixed engagement with said second shaft.

17. Apparatus according to claim 16 and further comprising deforming apparatus which imparts reciprocating motion to said second shaft.

18. Apparatus according to claim 15, and wherein said wire moves said deformable scraper from a stowed position to an undeformed deployed position and from said undeformed deployed position to a deformed deployed position.

19. Apparatus according to claim 18 and wherein said deformable scraper scrapes in a substantially rearward and forward motion.

20. Apparatus according to claim 1, and wherein said suction device is a syringe.

21. Apparatus according to claim 1, and wherein said suction device is coupled to a motor and a biasing device which create a sucking force in said suction device.

22. Apparatus according to claim 1, and wherein said suction device is a pump.

23. Apparatus according to claim 1, and wherein said uterine tissue collector further comprises a plurality of markings adapted to indicate the penetration of the uterine tissue collector into said uterus.

24. Apparatus according to claim 23 and wherein said markings are ruled.

25. Apparatus according to claim 23 and wherein said markings are coded by different colors.

26. Apparatus according to claim 23 and wherein said markings are coded by different shadings.

27. Apparatus according to claim 1, and wherein said uterine tissue collector further comprises a collector adapted to collect the sucked material.

28. Apparatus according to claim 27, and wherein said collector comprises a separator and a basin, said separator diverting sucked material from said suction device to said basin.

29. A method of collecting uterine tissue from a uterus comprising the steps of:
   inserting a deformable scraper through a cervical canal into said uterus, said scraper being capable of being deformed from an undeformed configuration to a deformed configuration;
   scraping said uterus by moving said deformable scraper between said undeformed configuration and said deformed configuration and sucking scraped material into a collector.

* * * * *